United States Patent
Shazly et al.

(10) Patent No.: US 10,016,302 B2
(45) Date of Patent: Jul. 10, 2018

(54) DIAGNOSTIC AND SURGICAL LASER DEVICE UTILIZING A VISIBLE LASER DIODE

(71) Applicant: VISUMEDICS, INC., Reading, MA (US)

(72) Inventors: Tarek A. Shazly, Pittsburgh, PA (US); Mark A. Latina, Reading, MA (US)

(73) Assignee: Visumedics, Inc., Reading, MA (US)

( * ) Notice: Subject to any disclaimer, the term of this patent is extended or adjusted under 35 U.S.C. 154(b) by 205 days.

(21) Appl. No.: 14/743,482

(22) Filed: Jun. 18, 2015

(65) Prior Publication Data

US 2015/0366713 A1    Dec. 24, 2015

Related U.S. Application Data

(60) Provisional application No. 62/014,568, filed on Jun. 19, 2014.

(51) Int. Cl.
| | |
|---|---|
| *A61F 9/008* | (2006.01) |
| *A61B 3/14* | (2006.01) |
| *A61B 3/12* | (2006.01) |
| *A61B 90/50* | (2016.01) |

(52) U.S. Cl.
CPC ............ *A61F 9/00821* (2013.01); *A61B 3/12* (2013.01); *A61B 3/14* (2013.01); *A61B 2090/502* (2016.02); *A61F 2009/00863* (2013.01)

(58) Field of Classification Search
CPC .......... A61B 3/14; A61B 3/12; A61F 9/00821
See application file for complete search history.

(56) References Cited

U.S. PATENT DOCUMENTS

| | | | |
|---|---|---|---|
| 4,499,362 | A | 2/1985 | Martin |
| 4,580,557 | A | 4/1986 | Hertzmann |
| 5,982,789 | A | 11/1999 | Marshall et al. |
| 6,090,102 | A | 7/2000 | Telfair et al. |
| 6,451,008 | B1 | 9/2002 | Frey et al. |
| 6,530,918 | B1 | 3/2003 | Ueno et al. |
| 7,115,120 | B2 | 10/2006 | Lin |
| 7,771,417 | B2 | 8/2010 | Telfair et al. |

(Continued)

FOREIGN PATENT DOCUMENTS

| | | |
|---|---|---|
| WO | WO 01/78830 A2 | 10/2001 |
| WO | WO 03/086322 A2 | 10/2003 |
| WO | WO 2015/195940 A1 | 12/2015 |

OTHER PUBLICATIONS

International Search Report for International Application No. PCT/US10/053013, dated Dec. 6, 2010.

(Continued)

*Primary Examiner* — Alyssa M Alter
(74) *Attorney, Agent, or Firm* — Sean D. Detweiler, Esq.; Morse, Barnes-Brown & Pendleton, P.C.

(57) ABSTRACT

System and method for providing diagnostic, imaging procedures and surgical laser treatments generating patterns of laser light on target tissue of a patient. The system includes aiming and treatment light beams originating from the same visible laser emitting diode, a scanner for generating patterns of points of light of the generated light, a controller, and a user interface that allows the user to select one of several possible point of light patterns, adjusts the point of light intensity and/or duration.

26 Claims, 23 Drawing Sheets

(56) References Cited

U.S. PATENT DOCUMENTS

| | | |
|---|---|---|
| 8,394,076 B2 | 3/2013 | Latina |
| 8,574,224 B2 | 11/2013 | Shazly et al. |
| 2003/0179344 A1 | 9/2003 | Van De Velde |
| 2004/0039378 A1 | 2/2004 | Lin |
| 2004/0116909 A1 | 6/2004 | Neuberger et al. |
| 2005/0080467 A1 | 4/2005 | Abe |
| 2005/0143720 A1 | 6/2005 | Yamada et al. |
| 2005/0203593 A1 | 9/2005 | Shanks et al. |
| 2005/0240168 A1 | 10/2005 | Neuberger et al. |
| 2006/0187978 A1 | 8/2006 | Telfair et al. |
| 2007/0121069 A1 | 5/2007 | Andersen et al. |
| 2007/0213693 A1 | 9/2007 | Plunkett |
| 2008/0015553 A1 | 1/2008 | Zacharias |
| 2008/0108983 A1 | 5/2008 | Nadolski |
| 2008/0252851 A1 | 10/2008 | Shazly et al. |
| 2008/0269847 A1 | 10/2008 | Nemenov |
| 2010/0318074 A1 | 12/2010 | Dacquay et al. |
| 2011/0075104 A1* | 3/2011 | Sakakibara .............. A61B 3/10 353/31 |
| 2011/0098692 A1 | 4/2011 | Shazly et al. |
| 2011/0306919 A1 | 12/2011 | Latina et al. |
| 2013/0237972 A1 | 9/2013 | Raksi |
| 2013/0261612 A1 | 10/2013 | Yokosuka et al. |
| 2013/0338649 A1 | 12/2013 | Hanebuchi et al. |
| 2013/0345683 A1 | 12/2013 | Mordaunt et al. |
| 2014/0121631 A1 | 5/2014 | Bean et al. |
| 2014/0228824 A1 | 8/2014 | Yee et al. |
| 2014/0243805 A1 | 8/2014 | Dick et al. |

OTHER PUBLICATIONS

International Search Report for International Application No. PCT/US2016/057500, dated Feb. 24, 2017.

International Search Report for International Application No. PCT/US2015/36469, dated Sep. 29, 2015.

* cited by examiner

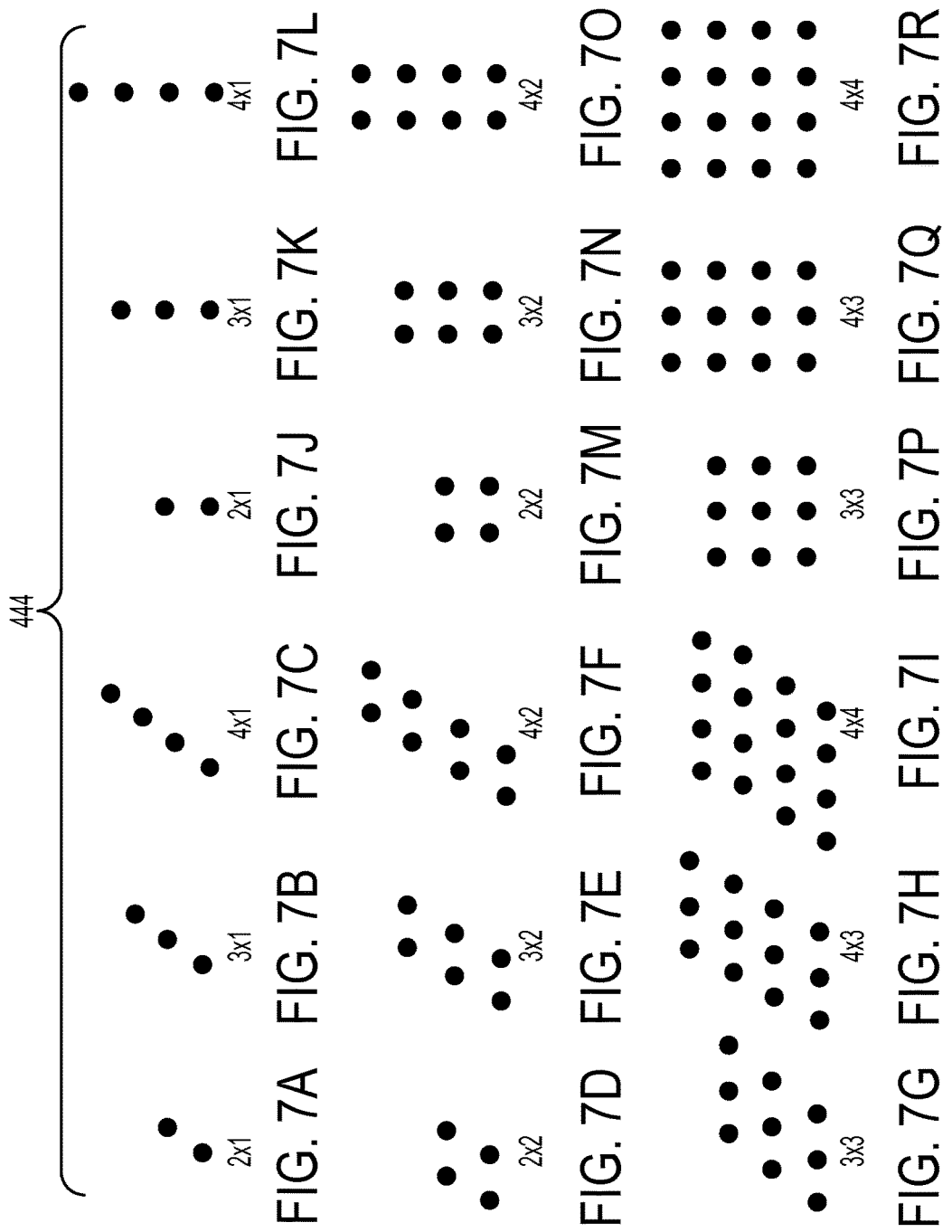

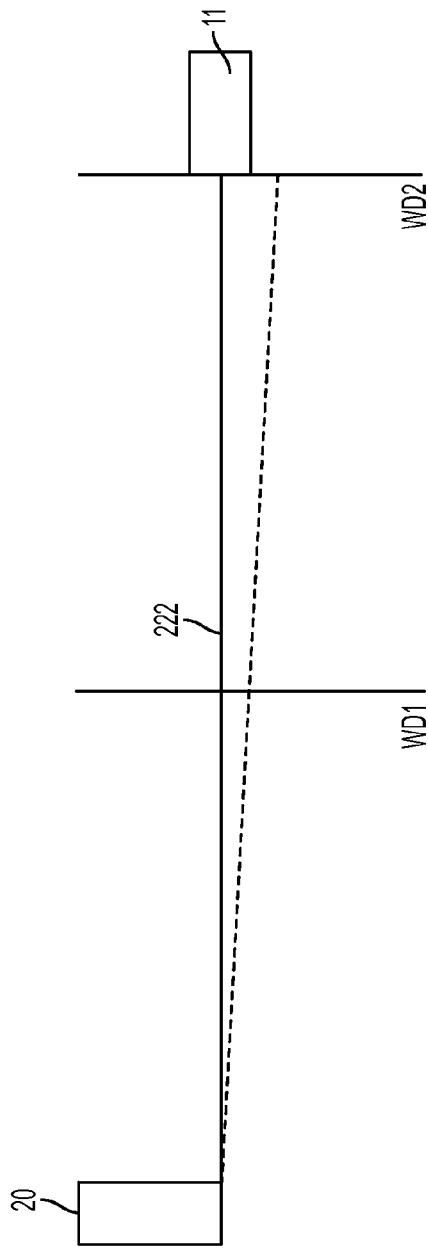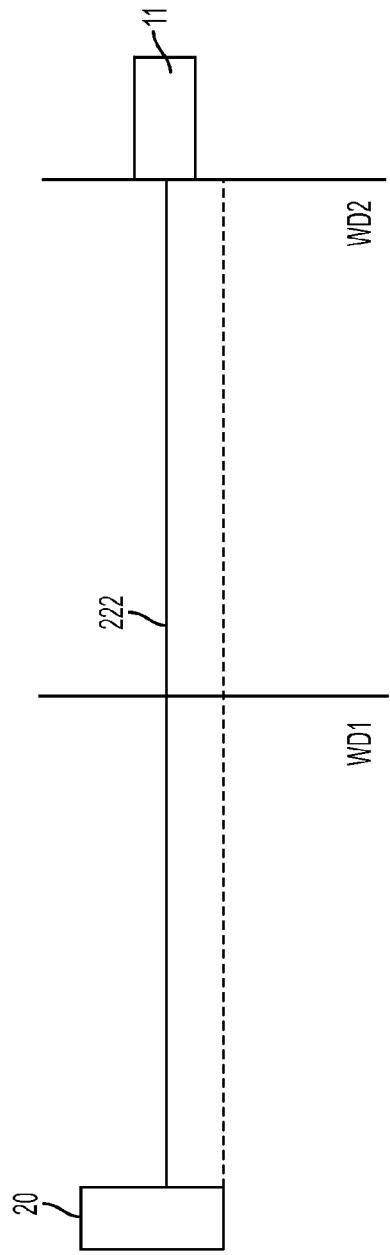

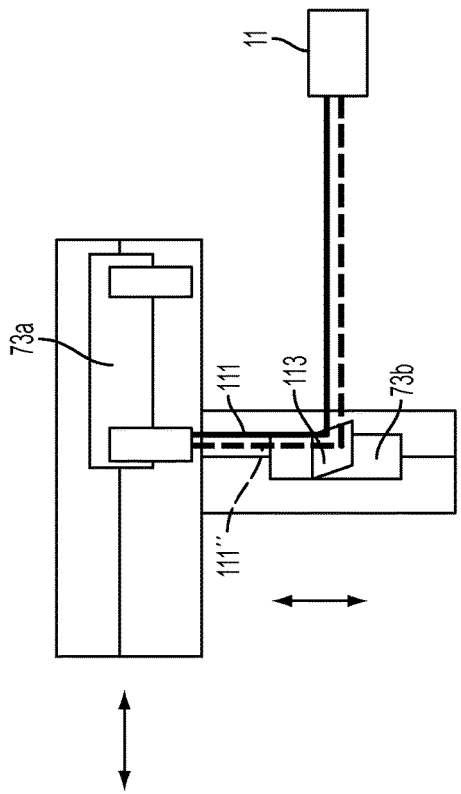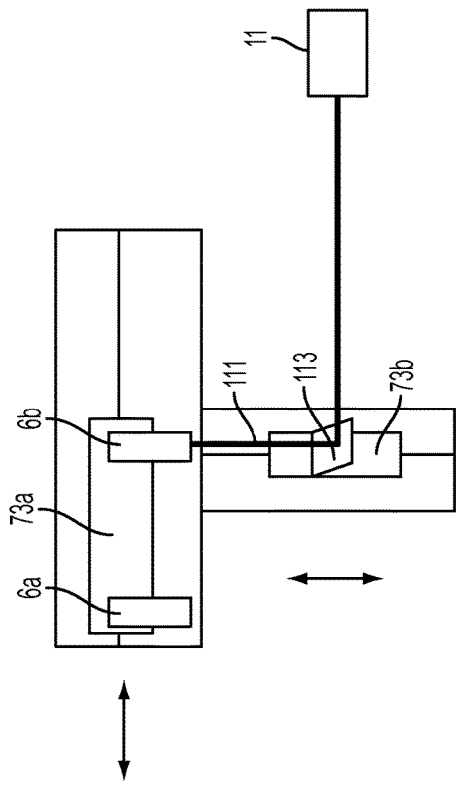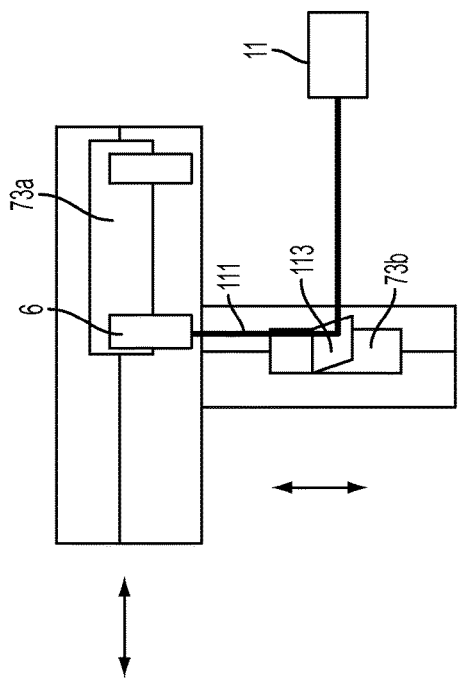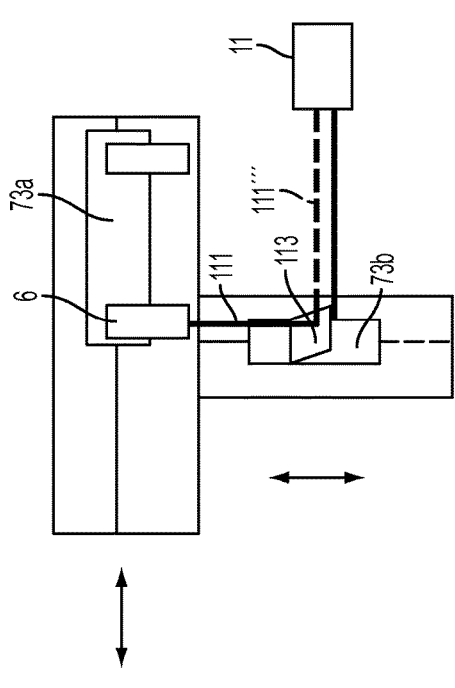

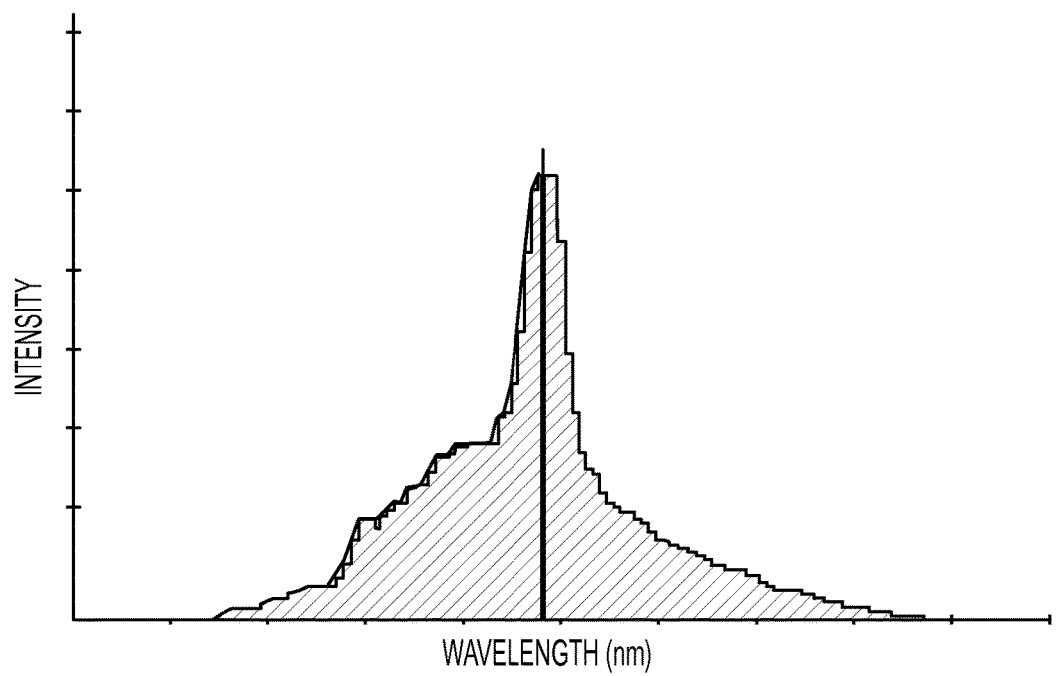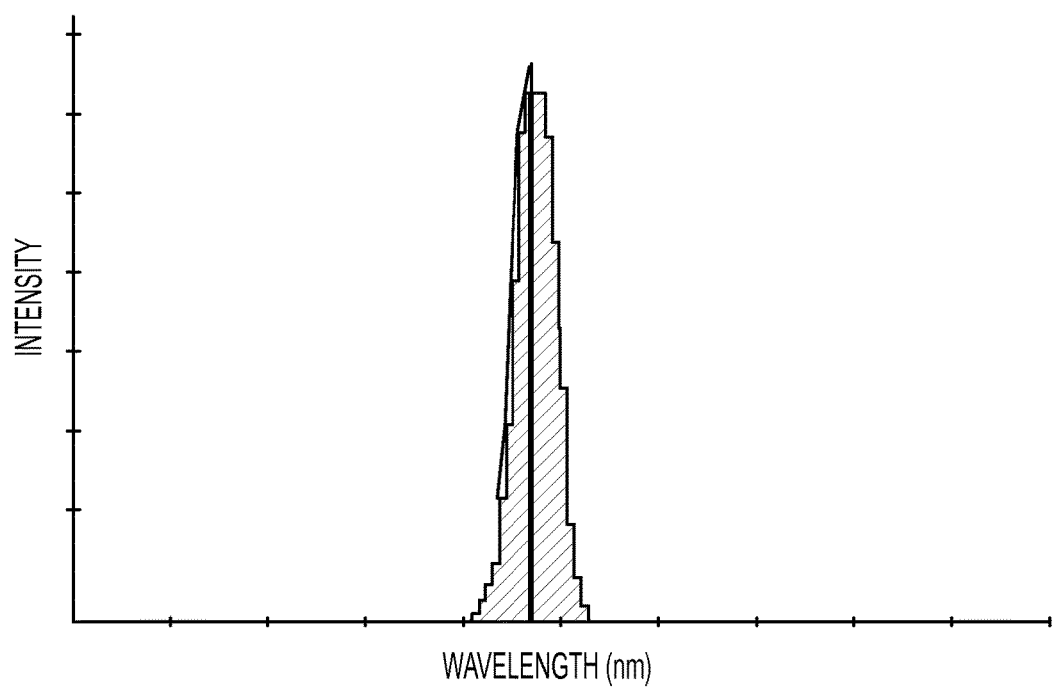
FIG. 22

DIAGNOSTIC AND SURGICAL LASER DEVICE UTILIZING A VISIBLE LASER DIODE

CROSS-REFERENCE TO RELATED APPLICATION(S)

This application claims priority to, and the benefit of, co-pending U.S. Provisional Application 62/014,568, filed Jun. 19, 2014, for all subject matter common to both applications. The disclosure of said provisional application is hereby incorporated by reference in its entirety.

FIELD OF THE INVENTION

The present invention relates to devices, systems and methods for providing diagnostic and data capture/documentation procedures and surgical laser treatments, and particularly, is directed to a compact visible laser device and beam pattern generator capable of diagnosing medical conditions and performing desired treatments, including but not limited to, single and or multi-point laser photocoagulation.

BACKGROUND

The complexities of conventional laser system designs used for the treatment of medical conditions of the eye hinder the attainment of requisite system functionality, as well as negatively impact system cost, size, and weight and increase the chances of system failure. Generally, in the current state of the art of photocoagulative laser surgery, for example, a treatment laser beam and an aiming light beam originate from two different sources, requiring a series of optical elements (and a substantial segment of expensive high maintenance fiber-optic cable to connect the main laser unit to its delivery system) for superposing both laser beams with the very high degree of precision needed for such procedures. This need to superimpose the aiming and treatment laser beam make it difficult to integrate existing laser devices with other complementary systems for diagnostic, data capture, and treatment purposes, resulting, at best, in cumbersome low mobility systems with low power efficiency and modest functionality. Better control and directing means are required in existing systems, as is the ability to enable temporally coincident treatments at multiple target locations and/or to enable the scanning of a treatment laser beam over time to multiple target locations. Current treatments allow only one point on a subject to be accessed when using, for example, a method such as laser indirect ophthalmoscopy. This is time consuming, especially when it comes to panretinal photocoagulation (PRP). Current laser treatment systems are also not equipped with diagnostic and/or data capture/documentation capabilities.

The current state of the art of pattern scanning lasers involves superimposing an aiming beam and a treatment beam with a pattern generator relying on galvomirrors, one inside the laser unit and two in the delivery system, such as found in US patent application number US 20130345683 A1 to Mordaunt, et al. The delivery system is connected to the laser unit via a fiber-optic cable. The first galvomirror projects the treatment beam into the inlet of a fiber-optic cable at the desired output during the whole period of scanning the laser pattern. The first galvomirror projects the beam toward the fiber-optic cable (ON time) to produce a laser burn and then shifts the beam away from the fiber (OFF time) where the laser power is wasted as it hits a dark barrier before the laser beam is re-directed toward the fiber-optic cable. During the OFF time, the last two galvomirrors move to a new position so that during the ON time the laser projects to a different location of the targeted tissue. The fact that the laser source is producing a treatment beam during the whole period of scanning a pattern into the targeted tissues, even when the treatment beam is not projected into the targeted tissues (OFF time), increases the power consumption by the laser system, increases the heat production, requires efficient active cooling, and shortens the life span of the laser source. Additionally, the power output of the laser is dependent on the very accurate projection of the treatment beam into the sub-millimeter (typically 0.1-0.2 mm) fiber-optic core. Any minor misalignment of the galvomirror can cause a major change in the output power of the laser. Also, the dimensions of the projected pattern are sensitive to the distance of the pattern generator from the targeted tissues, i.e. the further away the targeted tissues are from the pattern generator, the larger the pattern projected. Some existing pattern generating lasers can deliver patterns of laser burns to the targeted tissues via a slit lamp delivery system, but when the laser indirect ophthalmoscope is used as a delivery system, the laser can be used as individual (single point) burns with no pattern generating capabilities. Furthermore, existing laser indirect ophthalmoscopes function only as delivery systems for photocoagulative lasers via a fiber-optic cable. Because of the complexity of such laser systems, they are too large and too heavy to be incorporated in a head worn laser indirect ophthalmoscope.

SUMMARY

There is a need for a simpler, compact, less expensive, and easier to manufacture system and method for medical diagnosis, documentation, and surgical laser treatment that can be used in ophthalmology, dermatology, vascular surgery, and similar fields and can be truly portable.

There is a need for a system and method that operates at a wavelength or wavelengths that is effective for a variety of treatments, including performing a number of different photocoagulation procedures.

There is a need for a laser system and method that does not require the complex power supply and control mechanisms or the cumbersome fiber-optic connections currently used during ophthalmological, dermatological, vascular and similar-type surgeries. Additionally, there is a need for a system and a method that provides medical diagnosis, documentation and surgical treatment in a compact portable unit.

There is also a need for a system that can provide treatment at multiple target locations while exhibiting simplified control and directing means.

The present invention is directed toward further solutions to address these needs, in addition to having other desirable characteristics. Specifically the present invention is directed to systems and methods for diagnosis of a medical condition of a subject, viewing/imaging and capturing images/data pertaining to the subject, and treating multiple targets on the subject, simultaneously or sequentially, using an illuminating light source, an aiming light beam and a treatment laser beam in conjunction with optical components that are configured and arranged uniquely with respect to each other and to at least one single visible laser emitting diode, resulting in a compact system with desired portability and novel functionality. The present invention is also directed to a novel beam pattern generator and the integration of the novel beam pattern generator into the diagnostic, documentation and treatment system in order to affect treatment at multiple locations on a subject.

An embodiment of the present invention is directed to a system for diagnosing and/or treating a medical condition of a subject. The system includes an optical system with an illuminating light source and a focusing lens for focusing light from the illuminating light source onto an inner portion of an eye of a subject. The system includes a laser unit comprising a laser diode assembly operable with a single laser source. The single laser source emits an aiming light beam and a treatment laser beam from an outlet of the laser unit. A focal point of the focusing lens and a focal point of the outlet are generally coincident. Additionally, the optical system and/or the laser unit are operably disposed on a headset apparatus, which is sized, dimensioned, and configured for mounting on the head of a user.

According to aspects of the present invention, the system can be configured to induce a photocoagulation process at a targeted location on the inner portion of an eye. The illuminating light source can be a binocular indirect ophthalmoscope. The focusing lens can be disposed on the headset apparatus. The focusing lens can be distal from the headset apparatus and freely movable relative thereto by a user. The system can include an imaging system for receiving, capturing, and/or displaying a focusable image of the inner portion of the eye. The focusing lens can be disposed within an imaging device that includes an ocular fundus camera. The illuminating light source can be a binocular indirect ophthalmoscope. The laser unit can be operable in the absence or presence of a fiber-optic cable connector. The single laser source can be a fiber-optic coupled laser emitting diode or other laser emitting source. The wavelength of the aiming light beam and the wavelength of the treatment laser beam can differ by less than 50 nm.

According to aspects of the present invention, the laser diode assembly can include numerous single laser sources, and/or the laser unit can include numerous laser diode assemblies.

An embodiment of the present invention is directed to a system for diagnosing and/or treating a medical condition of a subject. The system includes an optical system with an illuminating light source and a laser unit with a laser diode assembly operable with a single laser source. The single laser source emits an aiming light beam and a treatment laser beam that follow generally the same light path. The system includes a focusing lens disposed to focus light onto an inner portion of an eye of a subject. The aiming light beam and the treatment laser beam pass through a beam pattern generator. The optical system and/or the laser unit and/or the beam pattern generator are operably disposed on a headset apparatus which is sized, dimensioned, and configured for mounting on the head of a user.

According to aspects of the present invention, the aiming light beam and the treatment laser beam can be generally collimated prior to passing through the beam pattern generator. Each of the aiming light beam and the treatment laser beam can be configured to produce a single point of light on the inner portion of an eye, a plurality of discrete points of light on the inner portion of an eye, at least one continuous pattern of light, or combinations thereof, on the inner portion of an eye. A point of light produced by the beam pattern generator can include a round, oval, square or other shaped form projected onto the inner portion of an eye.

According to aspects of the present invention, the system can include a control unit and/or remote interface configured to provide a user with control of a position and a characteristic of a pattern of beams exiting the beam pattern generator. The beam pattern generator can generate each one of a plurality of selectable patterns. Each pattern can include at least one of a plurality of points of light. The intensity of each one of the plurality of points of light can be adjustable via a user interface and a duration of incidence of each of the points of light upon the inner portion of the eye of a subject can be adjustable.

According to aspects of the present invention, a portion of the aiming light beam can be reflected by a dichroic mirror and a portion of the aiming light beam can pass through the focusing lens to illuminate the inner portion of an eye.

An embodiment of the present invention is directed to a beam pattern generator that includes a set of optical components configured and arranged to affect a displacement of an aiming light beam and a treatment laser beam along an inner portion of an eye of a subject. The aiming light beam and the treatment laser beam exiting the beam pattern generator are generally parallel to the aiming light beam and the treatment laser beam entering the beam pattern generator.

According to aspects of the present invention, the displacement of a beam of light along a distal target can be generally unaffected by a working distance. The set of optical components included in the beam pattern generator can include an active reflective element and a passive reflective element. The set of optical components can include two reflective elements, where a first reflective element and a second reflective element are mounted on an element carrier such that separate points of and/or a continuous pattern of light can be created. The set of optical components can include a lens element and a rotatable prismatic element. The set of optical components can include two lens elements, wherein a first lens element is movable in one direction and the second lens element is movable in a perpendicular direction and wherein the optical axis of the first lens element and an optical axis of a second lens element are parallel. A first and a second reflective element can be in optical communication with a prism. The set of optical components can include a first rotatable prismatic element and a second rotatable prismatic element. A surface of a first reflective element can be configured parallel to a surface of a second reflective element such that an optical beam is directed to different positions on the inner portion of an eye of a subject. A first and a second reflective element can be in optical communication with a prism. The set of optical elements can be mounted on a movable stage, wherein the movable stage can be connected to a laser diode assembly generating the aiming light beam and the treatment laser beam and can enable a position of a point of light on an inner portion of an eye of a subject to be affected without requiring movement of a component in the set of optical components.

According to aspects of the present invention, the beam pattern generator can be operably disposed on a headset apparatus, which is sized, dimensioned, and configured for mounting on the head of a user.

According to aspects of the present invention, the beam pattern generator can be operably coupled to a slit-lamp attachable laser, a fundus camera laser, a handheld laser ophthalmoscope, and/or another apparatus from which the aiming light beam and/or the treatment laser beam incidence upon the beam pattern generator. The another apparatus can include a laser emitting diode mounted on a first movable stage, where the first movable stage is movable in a direction that is perpendicular to a direction of motion of a second movable stage. A reflective element can be mounted on the second movable stage. The first movable stage can include more than one laser emitting diode. Each one of the more than one laser emitting diodes mounted on the first movable stage can emit a treatment laser beam with a characteristic wavelength that is not substantially the same as the characteristic wavelength emitted by a second of the more than one laser emitting diodes mounted on the first movable stage.

According to aspects of the present invention, the system can include an erector device, wherein the erector device includes a set of reflective elements and/or prisms configured so that an image is vertically and laterally reversed.

An embodiment of the present invention is directed to a system for diagnosing and/or treating a medical condition of a subject using a system that includes an optical system with an illuminating light source and a laser unit with a laser diode assembly that operates with a single laser source. The single laser source emits an aiming light beam and a treatment laser beam that follow generally the same optical path. The system includes a beam pattern generator. At least a portion of the aiming light beam and the treatment laser beam coupling with and/or passing through the beam pattern generator and coupling with and/or passing through a focusing lens can be disposed at a plurality of positions on an inner portion of an eye of a subject. The optical system and the beam pattern generator is operably disposed on a headset apparatus, which is sized, dimensioned, and configured for mounting on the head of a user.

According to aspects of the present invention, the laser diode assembly can include a plurality of single laser sources. Each single laser source can emit an aiming light beam and a treatment laser beam that follow generally the same light path as each other. The at least one laser diode assembly can be coupled to the focusing lens. The beam pattern generator can produce a pattern of light on the inner portion of the eye of a subject, where the pattern includes a plurality of points of light that are generated sequentially and/or where the pattern includes a plurality of points of light that are generated simultaneously. According to aspects of the present invention, a first laser emitting diode and a second laser emitting diode can produce an aiming beam simultaneously and/or sequentially.

An embodiment of the present invention is directed to a method for diagnosing and/or treating a medical condition of a subject by illuminating an inner portion of an eye of a subject and incidencing an aiming light beam and a treatment laser beam on at least one of a plurality of positions on the inner portion of an eye of a subject using an optical system and/or a laser unit that is operably disposed on a headset apparatus. A position is generally the same for the aiming light beam and the treatment laser beam. The headset apparatus is sized, dimensioned, and configured for mounting on the head of a user.

According to aspects of the present invention, a position is generally the same for the aiming light beam and the treatment laser beam. An aiming light beam and a treatment laser beam are incident on at least one of a plurality of positions on the inner portion of an eye of a subject. The aiming light beam and the laser treatment laser beam can be multiplied spatially and/or temporally to produce a pattern of points of light on the inner portion of an eye of a subject. At least one of a plurality of positions is accessible using a beam pattern generating device and/or a plurality of laser emitting diode sources.

In an embodiment of the present invention, a method for diagnosing and/or treating a medical condition of a subject includes disposing each of a plurality of aiming light beams on a plurality of positions on an inner portion of an eye of a subject, accessing a position by the shifting of each aiming light beam incidencing upon an inner portion of an eye in at least one direction via an intermediate image created by the focusing lens.

According to aspects of the present invention, a portion of the aiming light beam is reflected by a dichroic mirror and a portion of the aiming light beam passes through the focusing lens to illuminate the inner portion of an eye.

BRIEF DESCRIPTION OF THE FIGURES

These and other characteristics of the present invention will be more fully understood by reference to the following detailed description in conjunction with the attached drawings, in which:

FIG. 7A provides a schematic illustration of a first example of a selectable pattern of light generated with a beam pattern generator, according to one embodiment of the present invention;

FIG. 7B provides a schematic illustration of a second example of a selectable pattern of light generated with a beam pattern generator, according to one embodiment of the present invention;

FIG. 7C provides a schematic illustration of a third example of a selectable pattern of light generated with a beam pattern generator, according to one embodiment of the present invention;

FIG. 7D provides a schematic illustration of a fourth example of a selectable pattern of light generated with a beam pattern generator, according to one embodiment of the present invention;

FIG. 7E provides a schematic illustration of a fifth example of a selectable pattern of light generated with a beam pattern generator, according to one embodiment of the present invention;

FIG. 7F provides a schematic illustration of a sixth example of a selectable pattern of light generated with a beam pattern generator, according to one embodiment of the present invention;

FIG. 7G provides a schematic illustration of a seventh example of a selectable pattern of light generated with a beam pattern generator, according to one embodiment of the present invention;

FIG. 7H provides schematic illustration of an eighth example of a selectable pattern of light generated with a beam pattern generator, according to one embodiment of the present invention;

FIG. 7I provides schematic illustration of a ninth example of a selectable pattern of light generated with a beam pattern generator, according to one embodiment of the present invention;

FIG. 7J provides schematic illustration of a tenth example of a selectable pattern of light generated with a beam pattern generator, according to one embodiment of the present invention;

FIG. 7K provides schematic illustration of an eleventh example of a selectable pattern of light generated with a beam pattern generator, according to one embodiment of the present invention;

FIG. 7L provides schematic illustration of a twelfth example of a selectable pattern of light generated with a beam pattern generator, according to one embodiment of the present invention;

FIG. 7M provides schematic illustration of a thirteenth example of a selectable pattern of light generated with a beam pattern generator, according to one embodiment of the present invention;

FIG. 7N provides schematic illustration of a fourteenth example of a selectable pattern of light generated with a beam pattern generator, according to one embodiment of the present invention;

FIG. 7O provides schematic illustration of an fifteenth example of a selectable pattern of light generated with a beam pattern generator, according to one embodiment of the present invention;

FIG. 7P provides schematic illustration of a sixteenth example of a selectable pattern of light generated with a beam pattern generator, according to one embodiment of the present invention;

FIG. 7Q provides schematic illustration of a seventeenth example of a selectable pattern of light generated with a beam pattern generator, according to one embodiment of the present invention;

FIG. 7R provides schematic illustration of an eighteenth example of a selectable pattern of light generated with a beam pattern generator, according to one embodiment of the present invention;

FIG. 9A is a schematic illustrating the dependence of a lateral displacement of a beam of light along a distal target on working distance, in other words, on the distance between the operational optical system and the target, when the beam of light exiting the optical system experiences an angular rotation relative to the direction of incidence;

FIG. 9B is a schematic illustrating the independence of a lateral displacement of a beam of light along a distal target on working distance, in other words, on the distance between the operational optical system and the target, when the beam of light exiting the optical system experiences a displacement along a direction perpendicular to the direction of incidence;

FIG. 19A is a schematic illustration of a beam pattern generator comprising a set of movable mounts disposed in a neutral position, according to one embodiment of the present invention.

FIG. 19B is a schematic illustration of a beam pattern generator comprising a set of movable mounts, with the first movable mount displaced relative to its neutral position, according to one embodiment of the present invention.

FIG. 19C is a schematic illustration of a beam pattern generator comprising a set of movable mounts, with the second movable mount displaced relative to its neutral position, according to one embodiment of the present invention.

FIG. 19D is a schematic illustration of a beam pattern generator comprising a set of movable mounts, with a first and a second laser diode assembly attached to the first movable mount, according to one embodiment of the present invention.

FIG. 22 is a chart illustrating a spectrographic comparative analysis of two laser emitting diodes, in accordance with aspects of the present invention.

DETAILED DESCRIPTION

Figure 1:
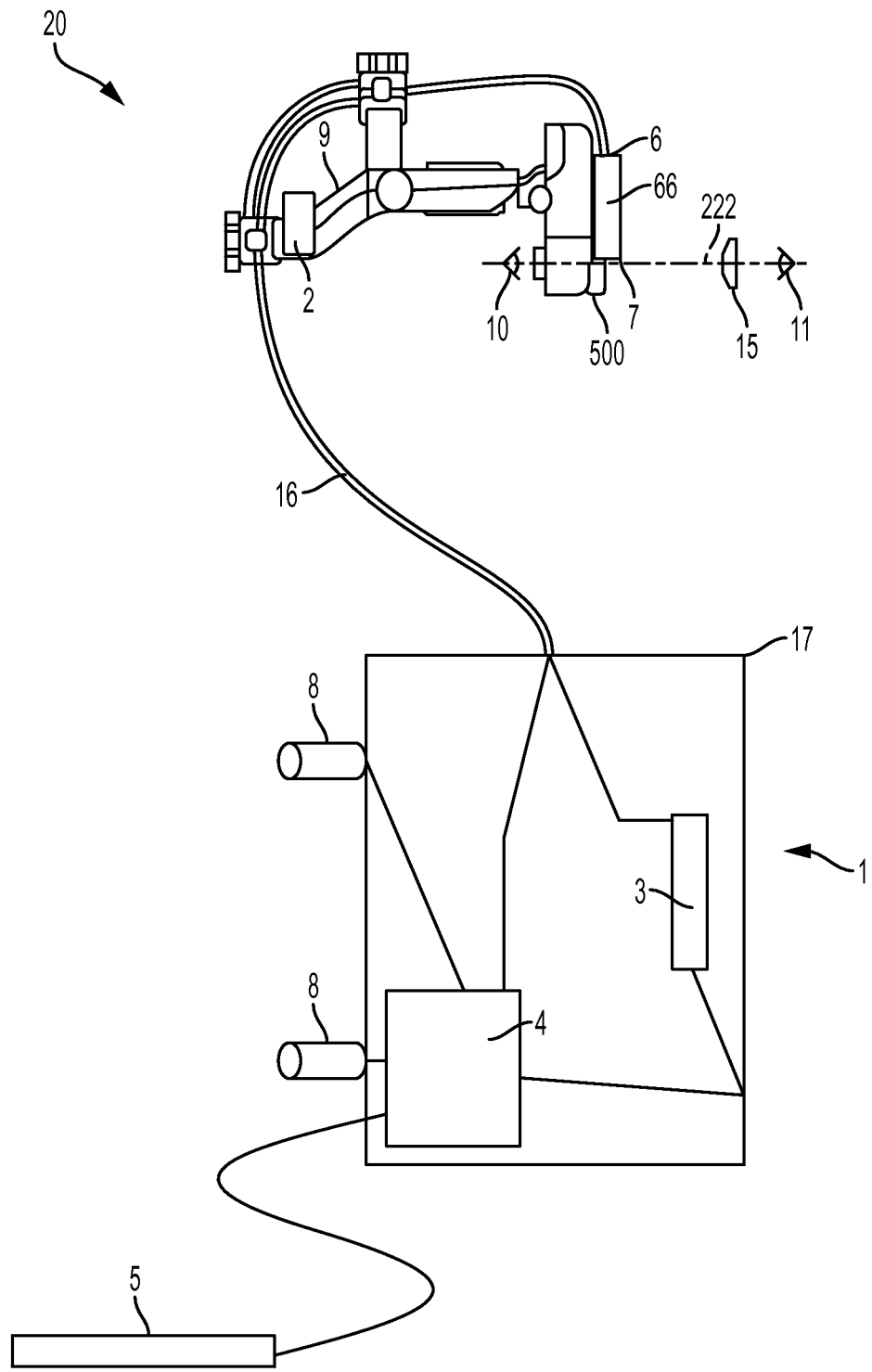
FIG. 1 is a schematic illustration of a compact surgical apparatus, according to one embodiment of the present invention.
Figure 2:
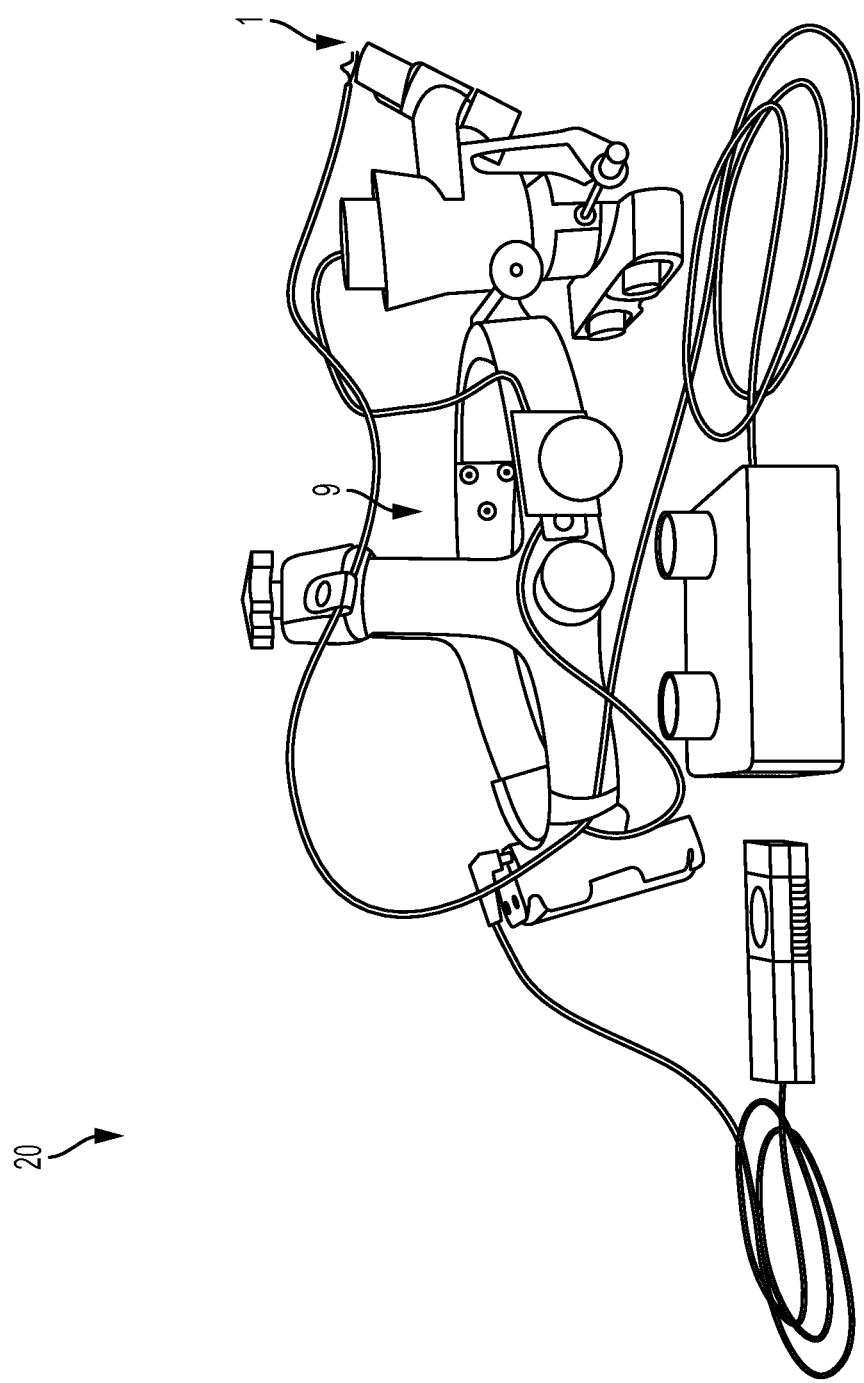
FIG. 2 is an image of a side view of a prototype compact surgical apparatus, according to one embodiment of the present invention.
Figure 3:
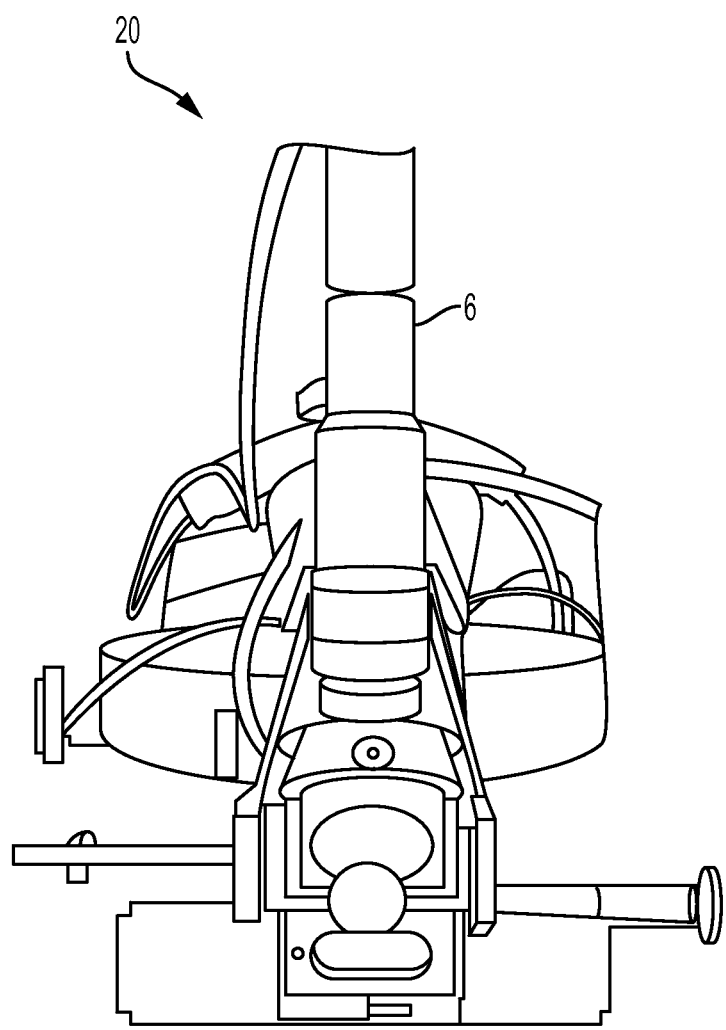
FIG. 3 is an image of a front view of the apparatus of FIG. 2, according to one aspect of the present invention.

An illustrative embodiment of the present invention relates to a compact surgical system which integrates a laser diode assembly with ophthalmic optical equipment in such a way that an aiming light beam and a treatment laser beam follow a shared path through the system and converge with an illuminating light beam at least at the target. Individual components of an operating optical system are configured and arranged in sufficient proximity to one another to enable the focal points of select components to be coincident. The ophthalmic surgical laser system can therefore be configured and arranged for mounting on the head of a user and for accommodating diagnosis and image/data capture and documentation. A compact surgical apparatus according to an embodiment of the present invention has viewing, imaging and laser treatment capabilities.

According to one embodiment of the present invention, viewing can be enabled by a head mountable viewing system that includes an illuminating light source projecting light into the eye of the subject, a headband with the illuminating light source attached, a focusing lens and any additional optical components such as reflective surfaces, lenses, and/or prisms. When the focusing lens is at an appropriate distance from the target, light from the illuminating light source can go through the focusing lens, illuminate the target and form an inverted reversed image of the target. The viewing system can, in one embodiment, split the inverted reversed image of the target into two images, at least partially correcting the orientation of each image and projecting one of the two at least partially corrected images onto a first ocular (e.g. Examiner's eye, display screen, etc.) and one of the two at least partially corrected images onto a second ocular (e.g. Examiner's eye, digital camera sensor, etc.).

In one embodiment the viewing system is a binocular indirect ophthalmoscope (a laser indirect ophthalmoscope), in an alternative embodiment the viewing system is an ocular fundus camera or a handheld ophthalmoscope. However, those of skill in the art will appreciate that a number of different alternatives to a binocular indirect ophthalmoscope may be utilized and are anticipated for use in conjunction with the present invention.

According to one embodiment of the present invention, imaging is enabled by a digital camera system mounted on, for example, the viewing system and directed toward the lens of the viewing system to allow capturing images and videos of the target prior to, during and/or after treatment. Such captured images or videos are stored, edited and/or shared using wired or wireless means using commercially available computer software. However, those of skill in the art will appreciate that a number of different alternatives to a digital camera may be utilized and are anticipated for use in conjunction with the present invention.

According to one embodiment of the present invention, treatment is affected with an aiming light beam and a treatment laser beam emitted from a single laser emitting diode source by a laser unit and directed via a laser outlet assembly along the same path as the illuminating light beam. In one embodiment of the present invention, the laser source generating both the aiming light beam and the treatment laser beam is a fiber-optic-coupled laser emitting diode. In one embodiment of the present invention, the fiber-optic coupled laser emitting diode can be a relatively short segment of fixed and/or non-detachable fiber-optic segment within the laser that is meant to be a light wave-guide. The fiber-optic segment is meant to act as a light wave-guide in order to further improve the characteristics of the laser beam. One of skill will appreciate that a variety of different types of laser sources and configurations can be used in lieu of and/or in addition to the single laser emitting diode.

Visible wavelengths, including but not limited to, for example, 405±20 nm, 445±20 nm, 635±20 nm, 658±20 nm, 577±20 nm, or 520±20 nm are readily generated and compatible with optics that can be used to focus and direct an aiming light beam, an illuminating light beam and/or a treatment laser beam according to embodiments of the present invention into a treatment area for visualizing, imaging and treating the target.

An illustrative embodiment of the present invention is directed to a beam pattern generator, which may be integrated into embodiments of the surgical laser system. The beam pattern generator affects parallel rather than angular displacement of a treatment laser beam exiting the pattern generator relative to an incident treatment laser beam, enabling the dimensions of each of a plurality of discrete points of light on a target to be consistently generated, independent of the distance between the operator and the subject.

The surgical laser system and/or beam pattern generator can be utilized for a variety of non-ophthalmic medical indications as well, in accordance with the invention described herein. Accordingly, the terms "target", "target tissue", "inner portion of the eye of a subject", and "subject's retina", used interchangeably herein.

The present invention includes new surgical treatment system designs providing high treatment laser beam quality with near-uniform fluence (energy density) that can directly be focused using lenses to produce a small single projected point of light (herein "point of light") of about 50-500 microns in width on a target, such as the inner portion of an eye of a subject. The ability to generate a treatment laser beam with a point of light width of about 100-200 microns provides the compact surgical apparatus with the ability to be utilized in treatments such as retinal photocoagulation. Other examples of treatments include, but are not limited to, focal and pan-retinal photocoagulation as well as laser retinopexy.

As an example, in part, due to portability and the ability to both diagnose and treat, an embodiment of the present invention can be used in diabetic retinopathy. Diabetic retinopathy is characterized by leakage from the retinal blood vessels resulting in retinal dot and blot hemorrhages, micro-aneurysms and exudates in early stages. Proliferative diabetic retinopathy, a later stage of the disease, is characterized by retinal neovascularization and vitreous or pre-retinal hemorrhages. While photocoagulative treatments can successfully treat diabetic retinopathy, and, in particular, pan-retinal photocoagulation is effective for causing regression of neovascular tissues, the present invention can diagnose and perform the same treatment procedure, in part due to the portability afforded by integration of the operating optical system, such as a binocular indirect ophthalmoscope, with the laser unit (laser indirect ophthalmoscope).

According to an illustrative embodiment of the present invention, a compact surgical system reduces the need for additional optical elements, as required by conventional surgical laser systems with similar capabilities, facilitating system construction and reducing production cost. System efficiency is improved, since the laser and light beams have a smaller number of glass-air and air-glass interfaces to cross, which are otherwise energy sinks in conventional devices prior to the present invention. The high energy efficiency of the visible laser emitting diodes makes it possible to utilize a simple power supply or batteries compared to the complex, large and heavy power supplies required to provide power to the currently available low efficiency diode pumped solid state lasers (DPSS) or gas lasers and to supply their cumbersome thermoelectric coolers. The compactness of the suggested laser system makes it possible to integrate it into an optical system such as an LIO to produce a self-contained diagnostic, imaging, laser therapeutic head worn truly portable unit.

These and other features of the invention will become apparent from the description which follows, given by way of example, with reference to the accompanying schematic drawings.

FIGS. 1 through 22, wherein like parts are designated by like reference numerals throughout, illustrate example embodiments of a compact surgical system 20 according to the present invention. Although the present invention will be described with reference to the example embodiments illustrated in the figures, it should be understood that many alternative forms can embody the present invention. One of ordinary skill in the art will additionally appreciate different ways to alter the parameters of the embodiment disclosed, such as the size, shape, or type of elements or materials, in a manner still in keeping with the spirit and scope of the present invention.

Turning to FIGS. 1 through 6, description of a compact surgical system 20 and corresponding method of use are provided. The compact surgical system 20 includes a laser unit 1 and an operating optical system 9. The laser unit 1 can include a power regulator 3, a laser diode assembly 6 with a laser emitting diode source, a timer circuit 4 and a laser trigger mechanism. The laser unit 1 emits energy in a wavelength within the visible spectrum, such as, for example, in the violet range, nominally 405±20 nm, the blue range, nominally 445±20 nm, the green range, nominally 520±20 nm, or the red range, nominally 635±20 nm or 658±20 nm or 577±20 nm. The laser diode assembly 6 includes, for example, a laser emitting diode 66 or laser emitting diode array. The figure further depicts an operator's eye 10 (e.g., the eye of the user of the apparatus) and a target 11 (e.g., the eye of the patient being treated). Additionally, the compact surgical system 20 includes means of image and or video capture such as a camera module 500 facing the treated eye 11. As utilized herein, the terms laser diode, laser emitting diode, laser emitting diode array and laser source are interchangeable. The laser diode assembly 6 further includes the laser emitting diode 66 housing, and can further include a heat sink and means to attach the laser diode assembly 6 to the laser outlet assembly 7.

According to one embodiment of the present invention, the operating optical system 9 includes a laser indirect ophthalmoscope, a fundus camera, slit-lamp and/or other apparatus that provides an illuminating light source and/or lens 15 in the operating optical system 9. In one embodiment of the present invention the lens 15 is a hand-held focusing lens. In an alternative embodiment the lens 15 is an objective lens of a fundus camera, a hand held slit lamp biomicroscopy lens (contact or non-contact) and/or a combination of said lenses. Accordingly the terms "lens", "lenses" and "lens system" are used interchangeably herein. The lens 15 is a lens of different refractive powers (+120 diopters to −60 diopters) and can be situated between the optical system 9 and the target 11. The lens 15 serves two main functions: focusing an illuminating light beam, an aiming beam and a treatment beam on the target 11 (the targeted tissue of the inner portion of the treated eye) and forming an intermediate image of the target 11 to be viewed by the optical system 9.

Lens 15 enables focusing an illuminating light beam from the operating optical system 9 and an optical beam 222 from the laser unit 1 and/or laser outlet assembly 7 on the target. The optical beam 222 can include the aiming light beam and/or the treatment laser beam. The laser unit 1 can emit the aiming light beam and the treatment laser beam both from the single laser emitting diode 66 through the laser outlet assembly 7. The lens 15 forms an image of the target 11 between the lens 15 and the optical system 9 that can be viewed by the examiner via the viewing oculars. A focal point of the laser outlet assembly 7 and the anterior focal point of the operating optical system 9 with lens 15 are configured to be confocal (meaning that the aiming light beam and the treatment laser beam emanating from the laser diode assembly 6 through the laser outlet assembly 7 and the anterior focal point of the illuminating light beam emanating from the operating optical system 9 have the same foci).

In accordance with embodiments of the present invention, lens 15 may be any one or any combination of a focusing lens, fundus viewing lens, objective lens, ophthalmic lens, or other type of lens. Additionally, lens 15 may be arranged for holding by hand, for attaching to the operating optical system 9, or in alternative arrangements according to embodiments of the present invention.

The laser unit 1 is attachable to an operating optical system 9 and can be located in a plurality of locations therein. For example, in an embodiment of the present invention, laser unit 1 is located inside the body of the binocular indirect ophthalmoscope or ocular fundus camera or attached to a beam splitter port therein. In one embodiment of the present invention, laser unit 1 is attachable to or located within an operating optical system 9 comprising a slit lamp device.

According to one embodiment, the laser power delivered and the pulse duration of the laser are determined by laser driving circuits, which provide precise digital control of the laser parameters without the need to use cumbersome complex optical elements. Other embodiments may include adaptors to endolaser probes, or may include a fundus camera that has already included in its structure the point of light size selection mechanism as described herein.

In an embodiment of the present invention, the laser outlet assembly 7 is a lens assembly including one or more lenses configured to focus the aiming light beam and the treatment laser beam. Additionally the laser outlet assembly 7 is capable of steering the laser beam.

A power source 2 provides the power to the compact surgical system 20. Those of skill in the art will appreciate that the power source 2 can take one of many forms including but not limited to a power supply box of the operating optical system 9 such as the battery box of a wireless binocular and (/or laser) indirect ophthalmoscope, a transformer or a battery providing the required power to drive the laser system, a standalone battery, rechargeable battery or another power source.

Electric current from the power source 2 passes to laser unit 1 through a power regulator 3, reducing the current to a level of, for example, between about 40-200 mA. The reduced current is sufficient to drive the laser emitting diode 66 at a sub-threshold level to emit a continuous broad band low energy visible light beam that is used as the aiming light beam. What is meant by a 'sub-threshold level' is that the laser emitting diode 66 is operating below its lasing threshold. The aiming light beam occurs at a laser emitting diode 66 baseline emission level of between about 0.1-2 mW. The timer circuit 4 is supplied with electric current from the power source 2. When the timer circuit 4 is activated, a predetermined adjustable pulse, or train of pulses, of relatively high current is supplied to the laser diode assembly 6, via a transmission line 16, to produce a pulse, or train of pulses, of the treatment laser beam. A "relatively high current" indicates that the current is herein the laser emitting diode threshold level. The timer circuit 4 is activated by triggering a laser switch 5, such as a hand or foot switch trigger which can either be wired or wireless.

In accordance with one embodiment of the present invention, laser controls 8 can be used by an operator to choose different laser parameters. For example, the laser controls 8 can send a signal to the timer circuit 4 to vary the laser pulses. The different controls for turning the laser on/off, switching from standby to ready mode, controlling the laser pulse power and duration are housed in a compact control unit 17 that can be attached to the side or the back of the optical operating system 9 via mechanical means such as a magnet or Velcro. Additionally the control unit 17 can have a text to speech engine to facilitate the change the laser parameters by the operator or the assistant without the need to have the user look at the actual settings on the control unit 17.

In accordance with one embodiment of the present invention, the pulse of the treatment laser beam can have a pulse duration within two sets or ranges, one in the nanosecond range (100 ns-100 microsecond) and another in a millisecond range (0.1 ms continuous). Other ranges are possible, depending on the desired treatment. The pulse current is significantly higher than the baseline current, to provide the laser emitting diode 66 with enough energy to produce a pulse of laser. For example, the pulse current can be between about 500-2000 mA for treatment purposes, versus a lower baseline level of between about 40-200 mA for aiming purposes. The characteristic of the treatment laser beam pulse(s) may depend on the pre-determined settings, as would be understood by those of ordinary skill in the art. The specific current levels are merely illustrative of an example implementation.

At the conclusion of the treatment laser beam pulse(s), the laser emitting diode 66 emission level returns back to the baseline of the aiming light beam supplied by the power regulator 3. The treatment laser beam emitted from the laser diode assembly 6 passes through a laser outlet assembly 7, which directs and controls the size and focus of the treatment laser beam. According to an embodiment, the laser outlet assembly 7 has a number of rheostats or switches to control the intensity and duration of the laser treatment beam pulse(s). According to an embodiment, the laser outlet assembly 7 includes one or more lenses, apertures, and/or prisms through which the laser energy passes.

One of skill in the art will appreciate that the narrow spectrum produced by the laser emitting diode 66 operating herein the threshold level satisfies the narrow band requirement of coherent laser light, whereas the broad spectrum produced by the laser emitting diode 66 operating at or below the threshold level does not qualify as a laser. Further the intensity of a below threshold beam, and "aiming light beam" is smaller than the threshold, or "treatment laser beam" and therefore better accommodates safety standards by decreasing potential retinal and other health related threats to operators who view emissions from the laser emitting diode 66 without eye protection and greatly increasing the permissible maximum viewing exposure. The aiming light beam is essentially harmless to users and readily viewable.

The various conventional components described herein and their constructions individually are well known to those skilled in the art and therefore will not be described in greater detail herein.

The laser unit 1 is attachable to the operating optical system 9. This enables the laser optical beam 222 and the operating optical system 9 to be confocal (meaning that the laser optical beam 222 and the anterior focal point of the operating optical system 9 have the same foci).

Figure 4:
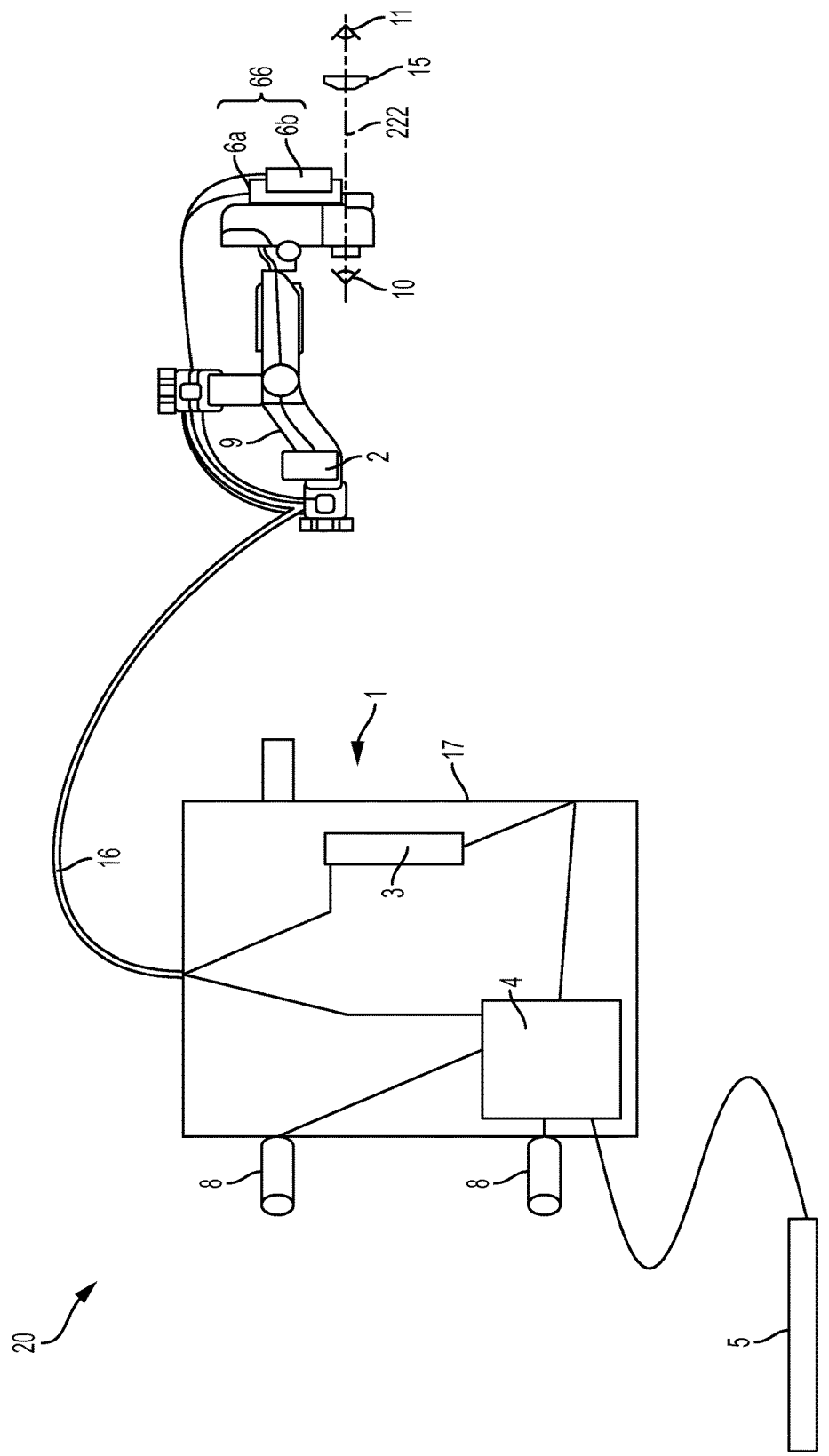
FIG. 4 is a schematic illustration of a compact surgical apparatus comprising a first and a second laser diode assembly, according to an embodiment of the present invention.

More than one laser emitting diode 66 emitting energy of the same or different wavelengths can be used as part of the compact surgical system 20. FIG. 4 shows the compact surgical system 20 embodying the present invention with a first laser emitting diode 66 and a second laser emitting diode 66. Each laser emitting diode 66 can be in the form of a single laser emitting diode or a laser emitting diode array. The laser unit 1 includes two laser diode assemblies 6a, 6b and emits energy in a wavelength within the visible spectrum, such as in the red or violet-blue, or green ranges.

An operator or physician determines the wavelength selected for treatment which in turn activates the laser emitting diode(s) 66 with the corresponding wavelength. An electric current between about 40-200 mA is sufficient to drive the laser diode assembly 6a to emit a continuous low energy visible aiming light beam in, for example, the green range 520 nm, or to drive the laser diode assembly 6b to emit a continuous low energy visible aiming light beam in, for example, the red wavelength range 600-700 nm. There may be separate power regulators 3, one for each laser diode assembly 6a, 6b, or a single power regulator 3 used by one laser diode assembly 6a, 6b at a time.

When the timer circuit 4 is activated, a predetermined adjustable pulse, or train of pulses, of relatively high current is supplied to the laser diode assembly 6a or 6b depending on the wavelength selected for treatment. A separate timer circuit 4 may be used for each laser diode assembly 6a, 6b, or the same circuit may be used on one laser diode assembly 6a, 6b at a time. The characteristic of the laser pulse(s) may depend on the pre-determined pulse settings, as would be understood by those of ordinary skill in the art.

To be clear, compact surgical system 20 differs from conventional ophthalmic laser systems at least in that in an embodiment of the present invention, each laser diode assembly 6a, 6b is capable of emitting both the aiming light beam and the treatment laser beam. The reason for different and separate laser diode assemblies 6a, 6b is to provide added capabilities relating to the wavelength and other laser characteristics while still having a single compact surgical system 20. This is not the same as conventional systems having a separate laser source for aiming and a separate laser source for treatment.

One of ordinary skill in the art will additionally appreciate that the herein description of two laser diode assemblies is merely representative of the concept of having a plurality of laser diode assemblies. As such, the present invention is not intended to be limited to one, or two, laser diode assemblies, but can include more. Each laser diode assembly, however, is intended to operate as described herein, where a single laser diode assembly has two power settings, such that both aiming and treatment laser beams can be emitted from the same source.

Figure 5:
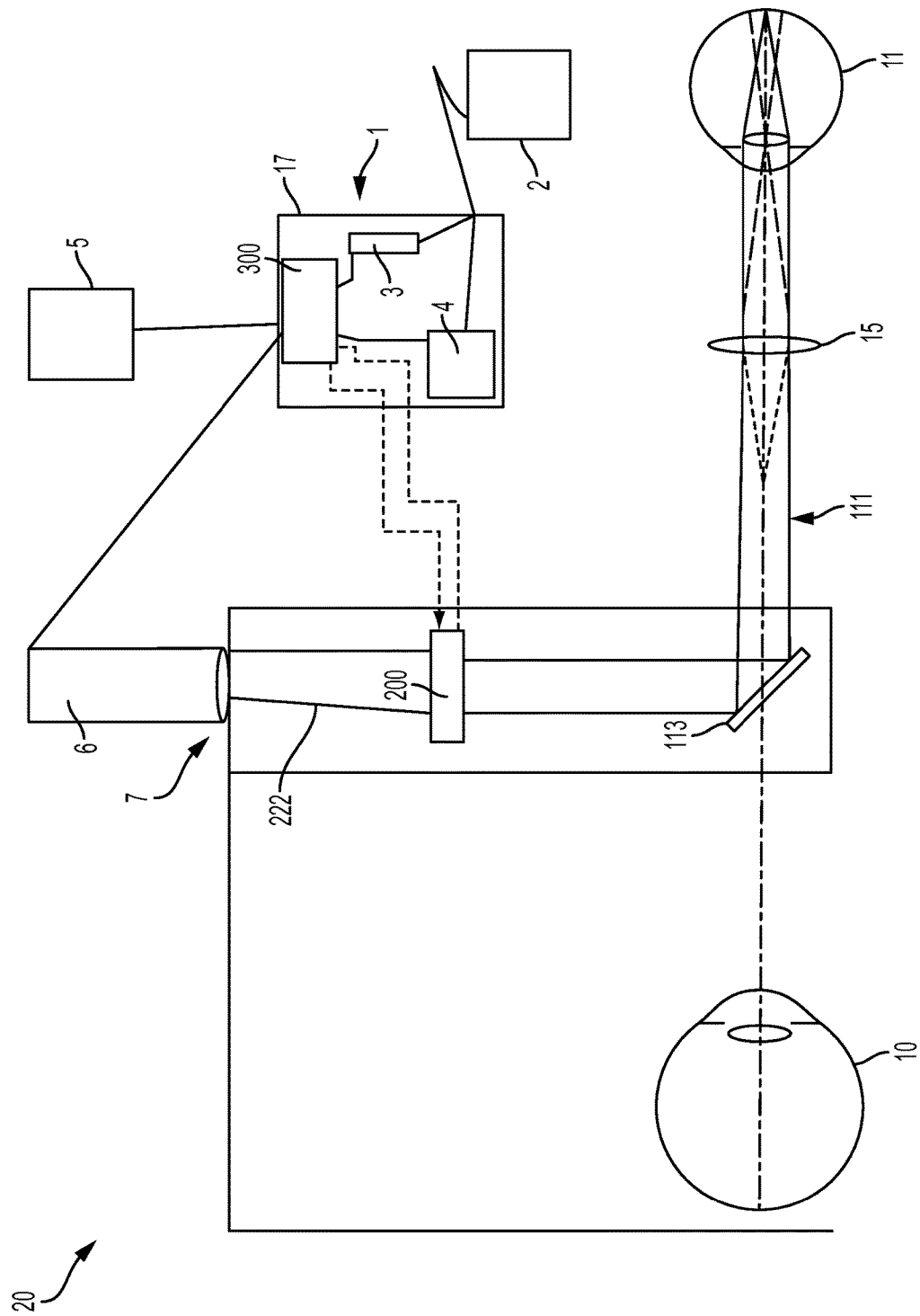
FIG. 5 is a schematic illustration of a compact surgical apparatus comprising a laser indirect ophthalmoscope including a beam pattern generator, according to an embodiment of the present invention.

FIG. 5 is a schematic diagram of a compact surgical system 20 in accordance with one embodiment of the present invention. The compact surgical system 20 includes the laser unit 1, and an operating optical system 9. At least a portion of the laser unit 1, for example the laser diode assembly 6, attaches to the optical operating system 9. An operator, such as a physician, wears the operating optical system 9 to view a target 11 with his/her eye 10 via or through lens 15. A processor 300 is coupled to the laser diode assembly 6 via the power regulator 3 to control light generation. The processor 300 may be a microprocessor, microcontroller, or any other type of suitable control electronics. In accordance with an embodiment of the present invention, multiple point of light laser therapy is enabled by incorporating a beam pattern generator 200 into the compact surgical system 20, allowing the physician to perform pan-retinal laser photocoagulation much faster, to treat patients in the supine position, and to add additional flexibility in operation to multiple point of light laser therapy. Processor 300 controls the visible laser emitting diode 66 (or multiple visible laser emitting diodes 66), of the laser diode assembly 6, via the power regulator 3 to create an optical beam 222, which is shown by dashed lines. The optical beam 222, which includes at least the aiming light beam and/or the treatment laser beam, upon being generated by the laser emitting diode 66, goes through the beam pattern generator 200 to mirror 113. Mirror 113 redirects the optical beam 222 toward lens 15 then the target 11.

For example, the beam pattern generator 200 can be integrated into an embodiment of the surgical laser system 20 in which the laser source generating the aiming light beam and the treatment laser beam is a single laser emitting diode source or in which a plurality of the aiming light beam and the treatment laser beam is generated by a plurality of single laser emitting diode sources. In one embodiment, the beam pattern generator 200 can be integrated into an embodiment of the surgical laser system with a slit lamp device, for example, for generating the illuminating light beam.

One of ordinary skill in the art will appreciate that, according to embodiments of the present invention, a first and a second visible laser emitting diode(s) 66, or a plurality of visible laser emitting diodes may be used in the compact surgical system 20 incorporating the beam pattern generator 200. Each component of the laser unit 1 with multiple laser emitting diodes, for example the power regulator 3 and the timer circuit 4, can be configured in the compact surgical system 20 in the singular or plural, as disclosed herein. Safety of the surgical apparatus is improved with the aiming light beam and the treatment laser beam originating from the same laser emitting diode and following the same optical path 111.

The beam pattern generator 200 projects aiming light beam onto the same position(s) on the target 11 as it does treatment laser beam. FIG. 7A through FIG. 7R illustrate each one of a plurality of alignment patterns 444 generated when the aiming light beam and/or treatment laser beam passes through the beam pattern generator 200. Each alignment pattern 444 coincides with portions of target 11 that will be treated with treatment laser beam, ensuring that the system is properly aligned to the portion(s) of target 11 in need of treatment. The beam pattern generator 200 produces an alignment pattern 444 having one and/or multiple points of light, where each point of light is generated simultaneously or consecutively.

Thus, as used herein, "beam multiplication" or "pattern generation" by beam pattern generator 200 applies to a system for affecting beam scanning across the target 11. Points of light and/or alignment patterns 444 are projected onto the target, each point of light being formed sequentially, with temporal and/or distal separation.

Each point of light of each alignment pattern 444 is spatially coincident with each one of a plurality of the target 11, so that when the laser emitting diode 66 energy goes from subthreshold to suprathreshold level, the alignment pattern 444 generated from the aiming light beam provides an outline of each one of a plurality of the target 11 to be treated. The projection of each point of light of the aiming light beam and each point of light of the treatment laser beam onto the target 11 composing the alignment pattern 444 may have a round shape, an oval shape, a square shape, or have some other form.

The beam pattern generator 200 enables multiple point of light laser therapy. Multiple point of light laser therapy is enabled when the optical beam 222 (which can switch) between the low energy aiming light beam and the higher energy treatment laser beam) is projected onto each of a plurality of points of the target 11 via the alignment pattern 444. Each of the plurality of points of projection can be aligned with each of a plurality of points of the target 11 needing treatment and be viewed by the operator. The aiming light beam and the treatment laser beam can produce a single point of light, multiple discrete points of light or continuous pattern(s) of light upon passing through the beam pattern generator 200.

In an embodiment of the present invention, the beam pattern generator 200 intercepts the relatively collimated optical beam 222 before it reaches the mirror 113 that further reflects the optical beam 222 onto the target 11. In an embodiment of the present invention, the operating optical system 9 receives the optical beam 222 and directs the optical beam 222 toward the target 11. The optical beam 222 originating from the laser diode assembly 6 can be slightly convergent so that it can be focused on the target 11. It can also be perceived by the patient.

The position and character of the pattern may be controlled by use of a control unit 17, for example a remote control panel and/or other user interface, such as graphical user interface (GUI). A pattern (which may be predetermined) is disposed at the target 11, for example at the patient's retina.

The mirror 113 is placed directly in the visualization path, such as a portion of the optical path 111 directed to the target 11, such as a user's eye, without much disturbance. In an alternative embodiment, mirror 113 is arranged in or near a center of the operating optical system 9, which could be, for example a binocular indirect ophthalmoscope, without substantially disturbing the visualization of the target 11 by the user. Visualization by the user of the target 11 is accomplished by viewing through or around the mirror 113.

Redirection of the optical beam 222 to form the alignment pattern 444 is affected in a number of ways, including but not limited to moving the laser diode assembly 6, moving the mirror 113, and/or using one or more moving optical elements.

The lens 15 creates a magnified intermediate image of the target 11 and aids visualization by the user of the target 11. In an embodiment, the lens 15 helps to position and focus each point of light in the alignment pattern 444 onto the target 11. Each point of light relayed to the target 11 will be magnified by the inverse of the image magnification of the lens 15. The lens 15 may be a contact lens that comes into contact with the target 11 or non-contact lens.

Figure 6A:
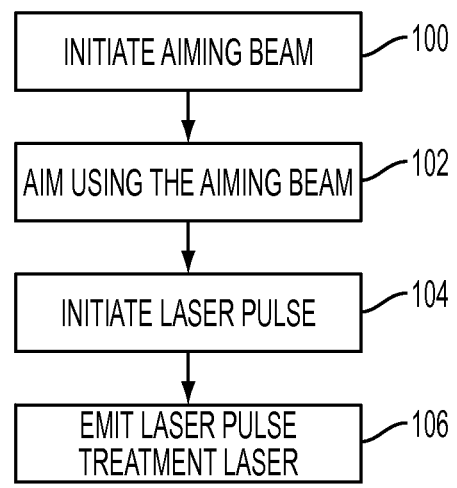
FIG. 6A is a flowchart illustrating by example a method of utilizing a compact surgical apparatus, according to one embodiment of the present invention.
Figure 6B:
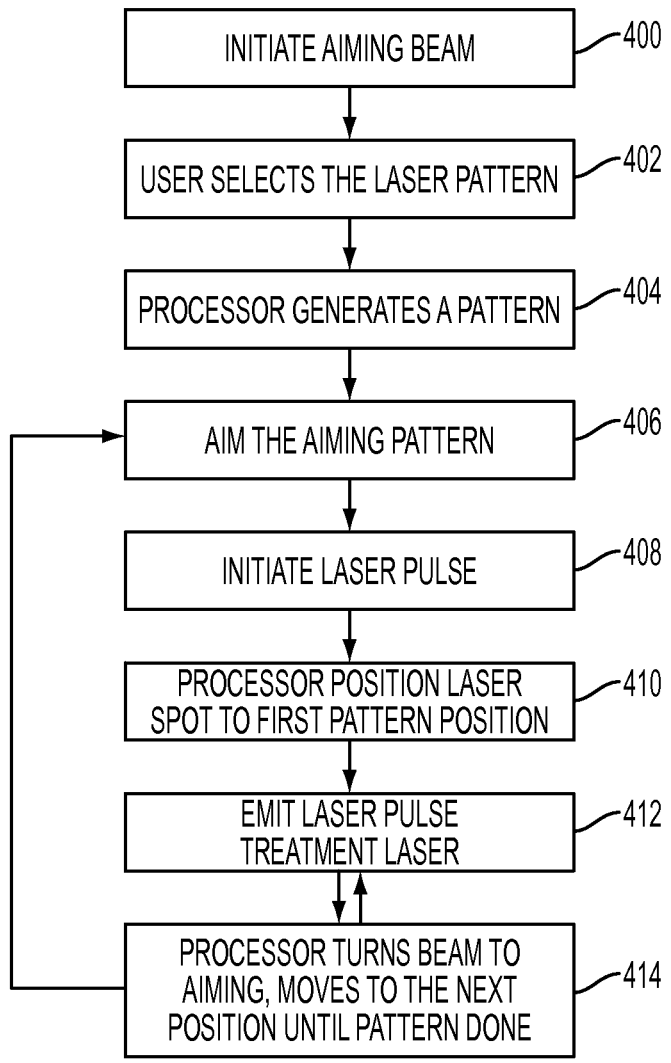
FIG. 6B is a flowchart illustrating by example a method of utilizing a compact surgical apparatus comprising a beam pattern generator, according to one embodiment of the present invention.

Turning now to FIG. 6A and FIG. 6B, a brief description of the method of utilizing the compact surgical system according to the present invention is illustrated. The method of use begins, as illustrated in FIG. 6A according to an embodiment of the present invention, (after any initial setup steps) with the provision of power to the laser diode assembly 6 of the laser unit 1 through the power regulator 3 to initiate the aiming light beam (step 100). The current is provided at a level sufficient to drive the laser emitting diode 66 to emit a continuous low energy visible laser beam that is used as the aiming light beam, and any necessary adjustments to the aiming light beam are made. The user utilizes the aiming beam to locate a desired area for treatment on the target 11, making any necessary adjustments to the laser beam at, for example, the laser outlet assembly 7 (step 102).

When a treatment laser beam is desired, the user activates the timer circuit 4 using the laser switch 5 (step 104). The timer is then supplied with electric current from the power source 2. When the timer circuit 4 is activated, a predetermined adjustable pulse, or train of pulses, of relatively higher current is supplied to the laser diode 6 and laser pulses emit in the direction of the target 11, producing a treatment laser beam (step 106).

The various conventional components described herein and their constructions individually are well known to those skilled in the art and therefore will not be described in greater detail herein.

Turning to FIG. 6B, according to an embodiment of the present utilizing the beam pattern generator 200, the user initiates the aiming beam (step 400) and selects one of a plurality of alignment patterns 444 (step 402) utilizing the control unit 17 and remote interface. The processor 300 sends a signal via the control unit 17 to generate an alignment pattern 444 (step 404). The user places the aiming beam so that the aiming beam projects the alignment pattern on the area of the target 11 to be treated according to the pattern selected by the user. The aiming light beam generating the alignment pattern 444 is aimed (step 406) at the target 11. The laser emitting diode 66 initiates a pulse of energy (step 408). The processor 300 positions the compact surgical system 20 such that at least one of a plurality of points of light comprising the alignment pattern 444 projects onto and is coincident with at least one of a plurality of positions on the target 11 for treatment. The treatment laser beam incidences (step 412) on the one of a plurality of positions on the target 11 needing treatment. The processor 300 directs the beam to a new one of a plurality of positions on the target 11 until points of light coincident with the selected alignment pattern 444 has incidenced (step 414) on the target 11.

FIG. 7A through FIG. 7R illustrate examples of a plurality of alignment patterns 444 that can be generated by the compact surgical system 20 according to an embodiment of the present invention. Each point of light that combines to form any one of the alignment patterns 444 is substantially equal in irradiance, size, and separation to any other point of light in the alignment pattern 444. The edge-to-edge separation distance, for example, between points of light typically varies from 0.5-3 times the point of light diameter which in turn varies from 50-500 microns with less than +/−10% irradiance variability.

FIGS. 7A, 7B, 7C, and 7J, 7K, and 7L show alignment patterns 444 in the form of linear arrays of points of light (e.g., 2×1, 3×1, 4×1). FIGS. 7D through 7I and 7M through 7R show alignment patterns 444 in the form of two-dimensional arrays (e.g., 2×2, 3×2, 4×2, 3×3, 4×3 and 4×4). Other alignment patterns 444 may also be generated, such as a circular alignment pattern 444 for encircling retinal tears. In an embodiment of the present invention, the beam pattern generator 200 is arranged in the operating optical system 9, for example a laser indirect ophthalmoscope, as shown in FIG. 5. The operating optical system 9 is worn by the user (e.g., physician, surgeon) using conventional head mounting hardware. The beam pattern generator 200 is controlled by the processor 300. Thus, in FIG. 5, the connection between the beam pattern generator 200 and the system is shown with solid black lines.

FIGS. 8-13 show embodiments of the beam pattern generator 200 that generates the alignment pattern.

Figure 8:
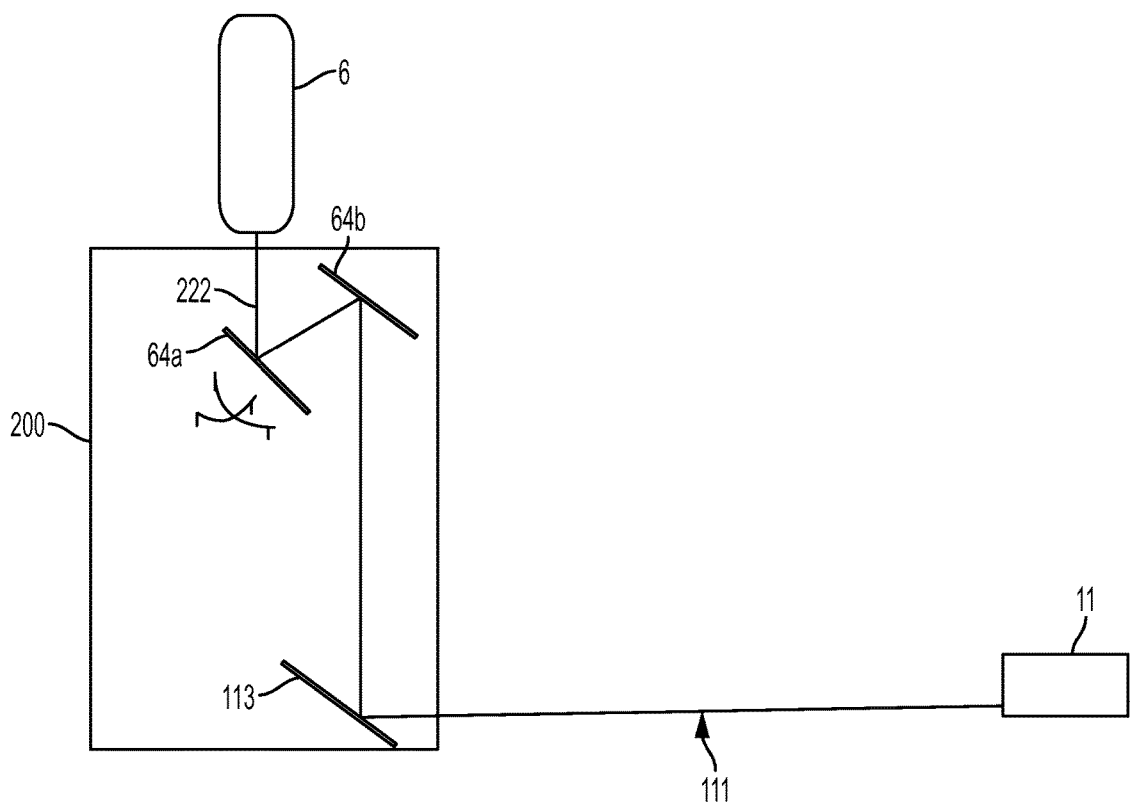
FIG. 8 is a schematic illustration of a beam pattern generator comprising a mirror, according to one embodiment of the present invention.

FIG. 8 is a schematic diagram of a first embodiment of the beam pattern generator 200. In this embodiment, the beam pattern generator 200 is made with one active component such as a Micro-electromechanical systems (MEMS) mirror. An active 2-axis MEMS mirror scanner 64a is capable of tilting both horizontally and vertically, and a passive mirror 64b. The optical beam 222 incidences upon the scanner 64a, which directs the optical beam 222 toward the passive mirror 64b. As the scanner 64a moves, it reflects the optical beam 222 in different directions. Optical beams 222 that are reflected in different directions strike the second mirror 64b at different locations, and are reflected by the second mirror 64b onto different locations on the mirror 113. The beams reach the mirror 113 at different points and are reflected toward the image of the target 11 provided by lens 15 as shown in FIG. 5. When the timing of the laser pulses is coordinated with the angular position of the scanning mirror 64a, separate beams (i.e., multiple points of light) are created. However, if the laser emitting diode 66 of the laser diode assembly 6 is left to run continuously, a likewise continuous alignment pattern 444 may be created.

In the prior art, commercially available laser devices capable of producing a laser pattern on the patient retina operate essentially using galvomirrors. Such galvomirrors are both cumbersome and require complicated driving circuits. Additionally, the galvomirror "tilting" turns the laser beam and hence the laser shots in one direction or the other by a pre-determined angle rather than a predetermined displacement. By knowing the distance between the laser outlet and the retina of the patient, the degree of spacing between the laser shots can be reliably produced by rotating the laser beam to a predetermined angle. This can be done when such a laser system is mounted to a slit lamp as slit lamps have a fixed working distance between the slit lamp and the targeted tissues of the eye. When using a laser indirect ophthalmoscope, the working distance is much more variable depending on multiple factors such as the user's accommodation and the power of the fundus lens used. This variability in working distance can lead to significant variability in the spacing of the laser shots if the beam "turning" method is utilized to scan a laser pattern into the patient's retina. Alternatively, utilizing laser beam displacement where the laser beam is displaced into a parallel path to the original beam path would provide more reliable, distance independent spacing of the points of light.

FIG. 9A illustrates the way in which a lateral displacement of an optical beam 222 along a distal target depends on working distance (WD1/WD2) when the beam of light exiting the operating optical system 20 experiences an angular rotation relative to the direction of incidence. In contrast, FIG. 9B illustrates the independence of a lateral displacement of optical beam 222 along a distal target 11 on working distance (WD1/WD2) when the optical beam 222 experiences a displacement along a direction perpendicular to the direction of incidence.

Figure 10:
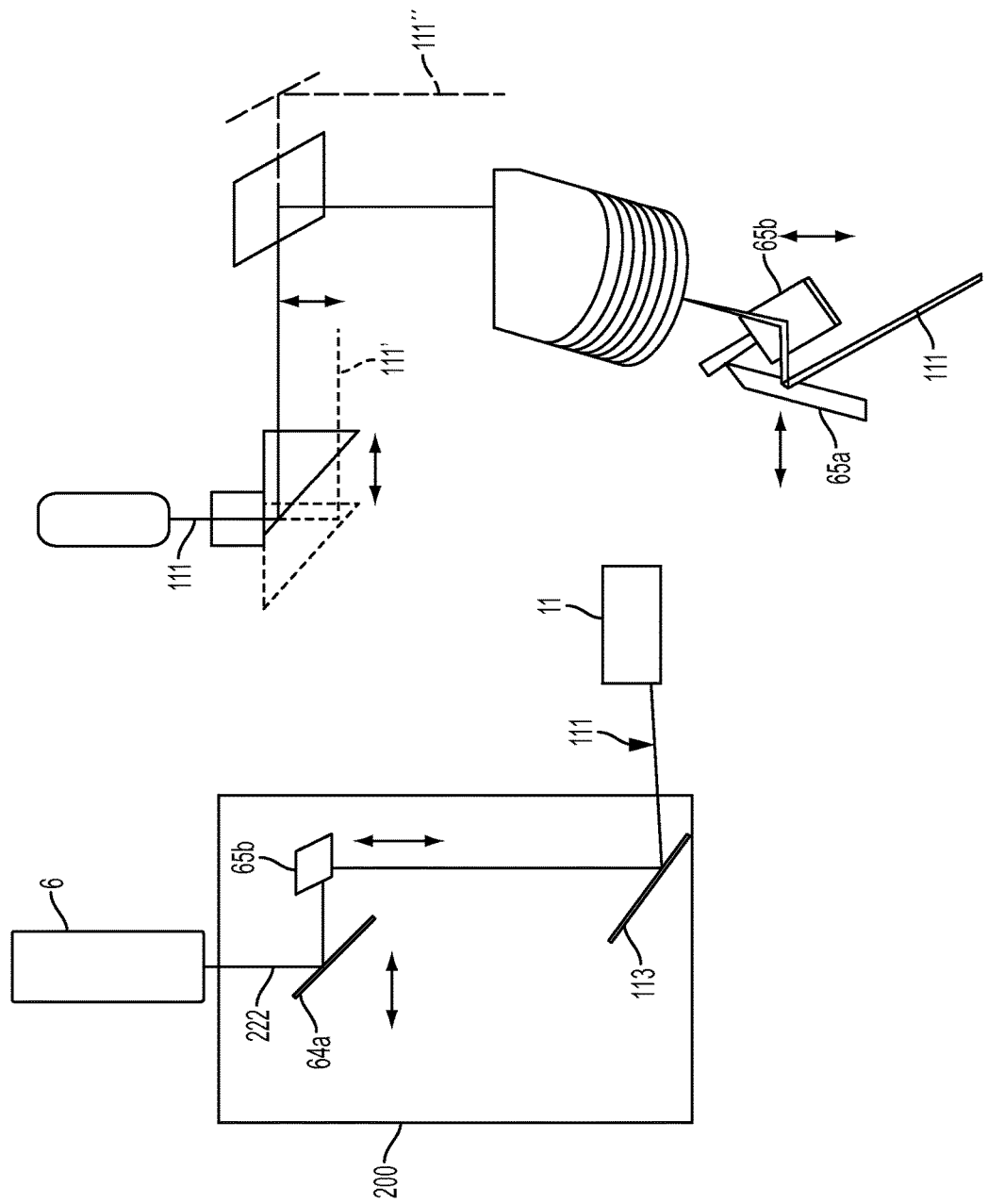
FIG. 10 is a schematic illustration of a beam pattern generator comprising a shifting mirror, according to one embodiment of the present invention.

FIG. 10 is a schematic diagram of an alternative embodiment of the beam pattern generator 200. In this embodiment, the beam pattern generator 200 is made with two movable reflective elements with reflective surfaces such as two mirrors 65a and 65b. The optical beam 222 incidences upon the first mirror 65a (or other reflective surface) and directs the optical beam 222 toward the second mirror 65b (or other reflective surface). As the mirror 65a moves in a perpendicular direction to the angle of incidence of the optical beam 222 in the horizontal direction, it reflects the optical beam 222 so that it is displaced in the horizontal axis to a parallel optical beam path 111' by a degree of displacement determined by the degree of displacement of the mirror 65a. Optical beams 222 that are reflected in different directions strike the second mirror 65b at different locations, and are reflected by the second mirror 65b onto different locations on the mirror 113. As the mirror 65b moves in a perpendicular direction to the angle of incidence of the optical beam 222 in the vertical direction, it reflects the optical beam 222 so that it is displaced in the vertical axis to a parallel optical beam path 111" by a degree of displacement determined by the degree of displacement of the mirror 65b.

The beams reach the mirror 113 at different points and are reflected toward the image of the target tissue provided by lens 15 as shown in FIG. 5.

When the timing of pulses of the laser emitting diode 66 is coordinated with the angular position of the mirrors 65a and/or 65b, which act as an optical beam 222 scanner, a plurality of optical beams 222 (i.e., multiple points of light) are created. However, if the laser emitting diode 66 of the laser diode assembly 6 runs continuously, a continuous alignment pattern 444 of points of light is created.

This embodiment, as disclosed herein, carries the advantage of producing a parallel shift in the optical beam 222 so that the distance between the points of light does not depend on the working distance as explained herein.

Figure 11:
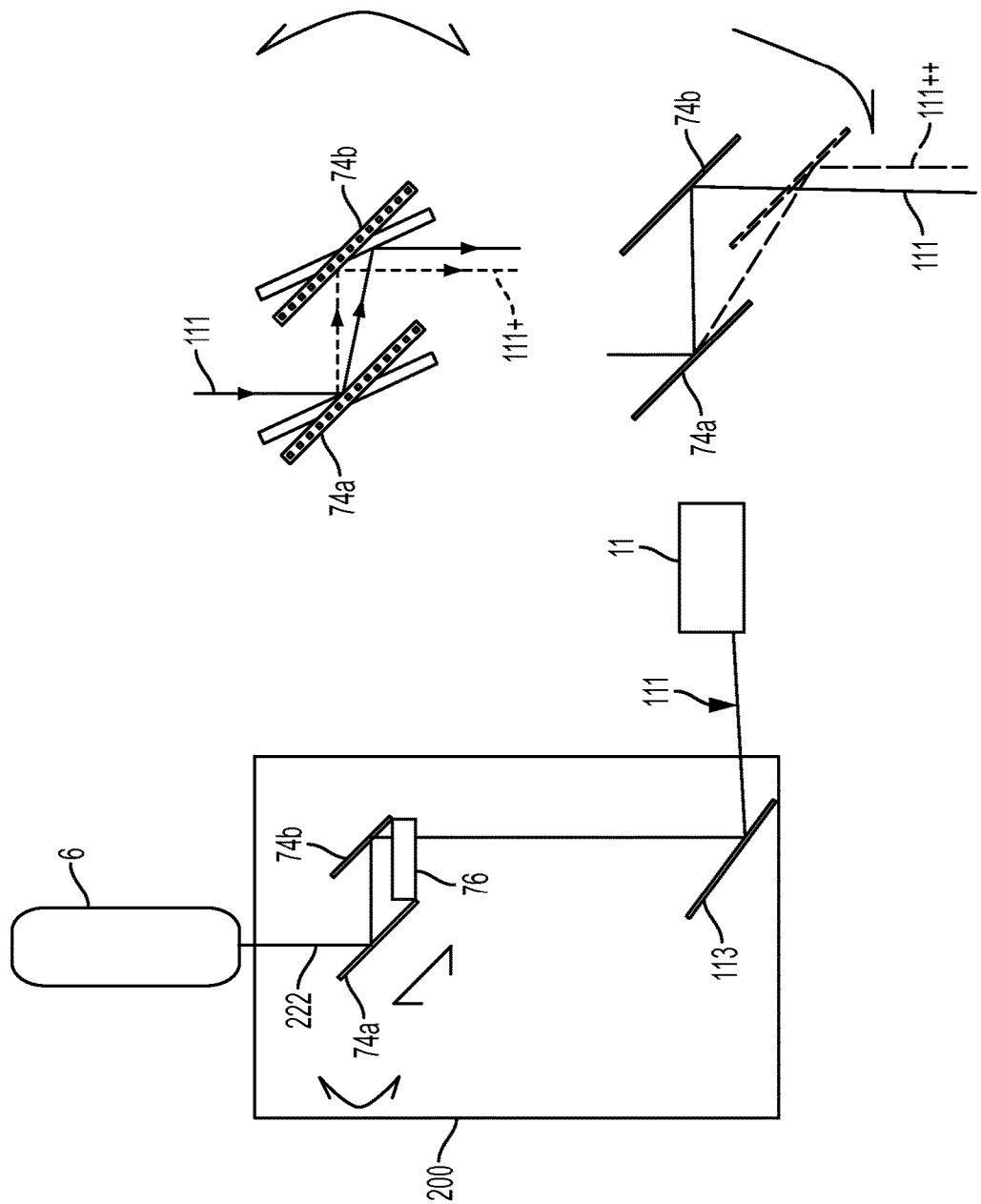
FIG. 11 is a schematic illustration of a beam pattern generator comprising an alternative shifting mirror, according to one embodiment of the present invention.

FIG. 11 is a schematic diagram of another embodiment of the beam pattern generator 200. In this embodiment, the beam pattern generator 200 is made with two reflective elements such as two mirrors 74a and 74b that are fixed to a common movable carrier 76 so that they are parallel. Alternatively a prism with two reflective surfaces 74a and 75b can be utilized. The element carrier 76 is capable of turning in two perpendicular directions both horizontally and vertically. The optical beam 222 incidences upon the first reflective surface 74a, which directs the optical beam 222 toward the second reflective surface 74b. As the carrier 76 turns vertically, the mirror 74a reflects the optical beam 222 so that it is displaced parallel to optical path 111+. Optical beams 222 that are reflected in different directions strike the second mirror 74b at different locations, and are reflected by the second mirror 74b onto different locations on the mirror 113. As the carrier 76 turns in a perpendicular direction, the optical beam 222 is reflected in a different vertically displaced optical path 111++. The beams reach the mirror 113 at different points and are reflected toward the image of the target 11 provided by lens 15 as shown in FIG. 5. When the timing of the laser pulses is coordinated with the angular position of the scanning mirror 74a and/or 74b, separate beams (i.e., multiple points of light) are created. However, as disclosed herein, if the laser emitting diode 66 of the laser diode assembly 6 is left to run continuously, a likewise continuous pattern may be created.

Figure 12:
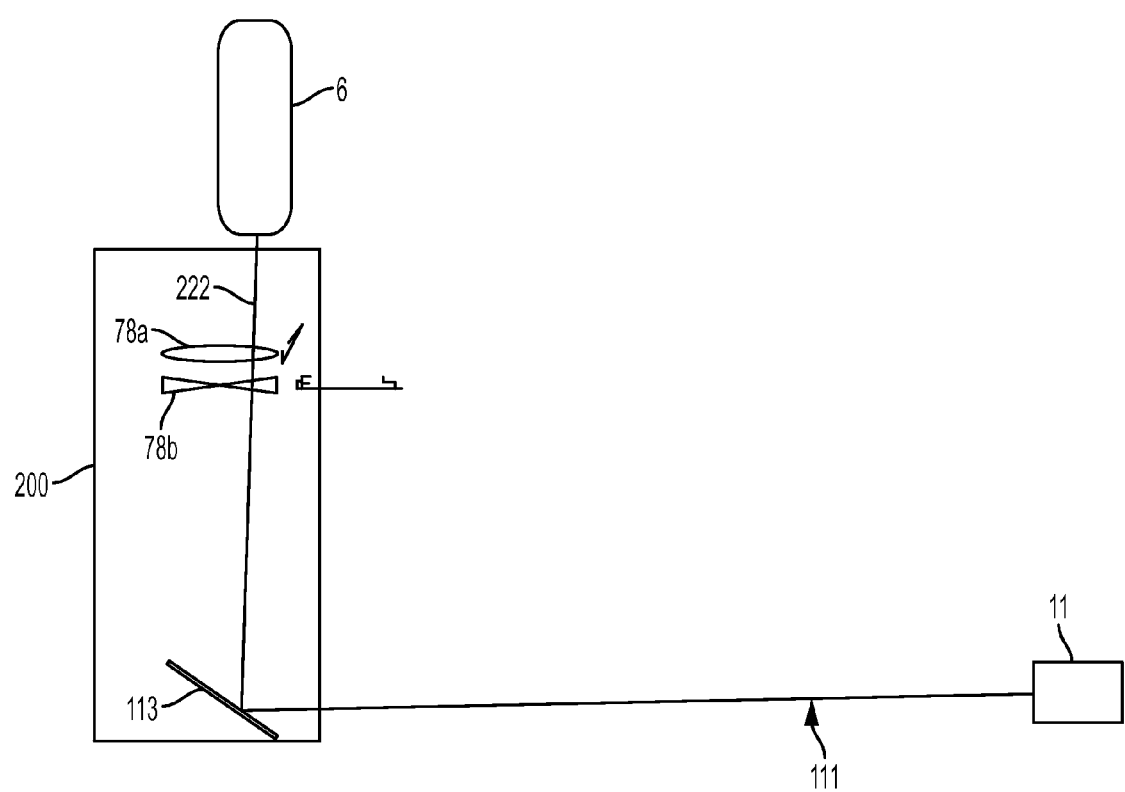
FIG. 12 is a schematic illustration of a beam pattern generator comprising a decentered lens, according to one embodiment of the present invention.

FIG. 12 is a schematic diagram of a second embodiment of the beam pattern generator 200. In this embodiment, the beam pattern generator 200 includes two lens elements, specifically a first plus powered moving lens 78a that is movable transversely perpendicular to its optical axis. The second minus powered lens 78b is stacked with the plus powered lens so that their optical axes are parallel. The second minus powered lens 78b is movable vertically perpendicular to its optical axis, such that the second minus powered lens 78b is movable in a perpendicular direction to the first plus powered moving lens 78a. As the lens 78a moves longitudinally along the axis, the optical beam 222 coming from the laser diode assembly 6 reaches different parts of the lens 78a, thus getting deviated in the horizontal axis differently depending on how far off the optical center of the lens 78a is encountered. It will also be refracted because of the plus power of the lens. The optical beam 222 then gets intercepted by the lens 78b. As the lens 78b moves in the vertical axis, the optical beam 222 coming from the laser diode assembly 6 reaches different parts of the lens 78b, thus getting deviated in the vertical axis differently depending on how far off the optical center of the lens 78b is encountered. It will also be refracted because of the minus power of the lens. The refractive powers of the plus powered lens 78a are neutralized by the minus powered lens 78b so that the total effect on the optical beam 222 focusing and magnification is negligible. The movements of both lens 78a and 78b are controlled by the processor 300 to direct the optical beam 222 to different positions on the mirror 113, to different positions on the lens 15, and to different areas of the target 11.

Figure 13:
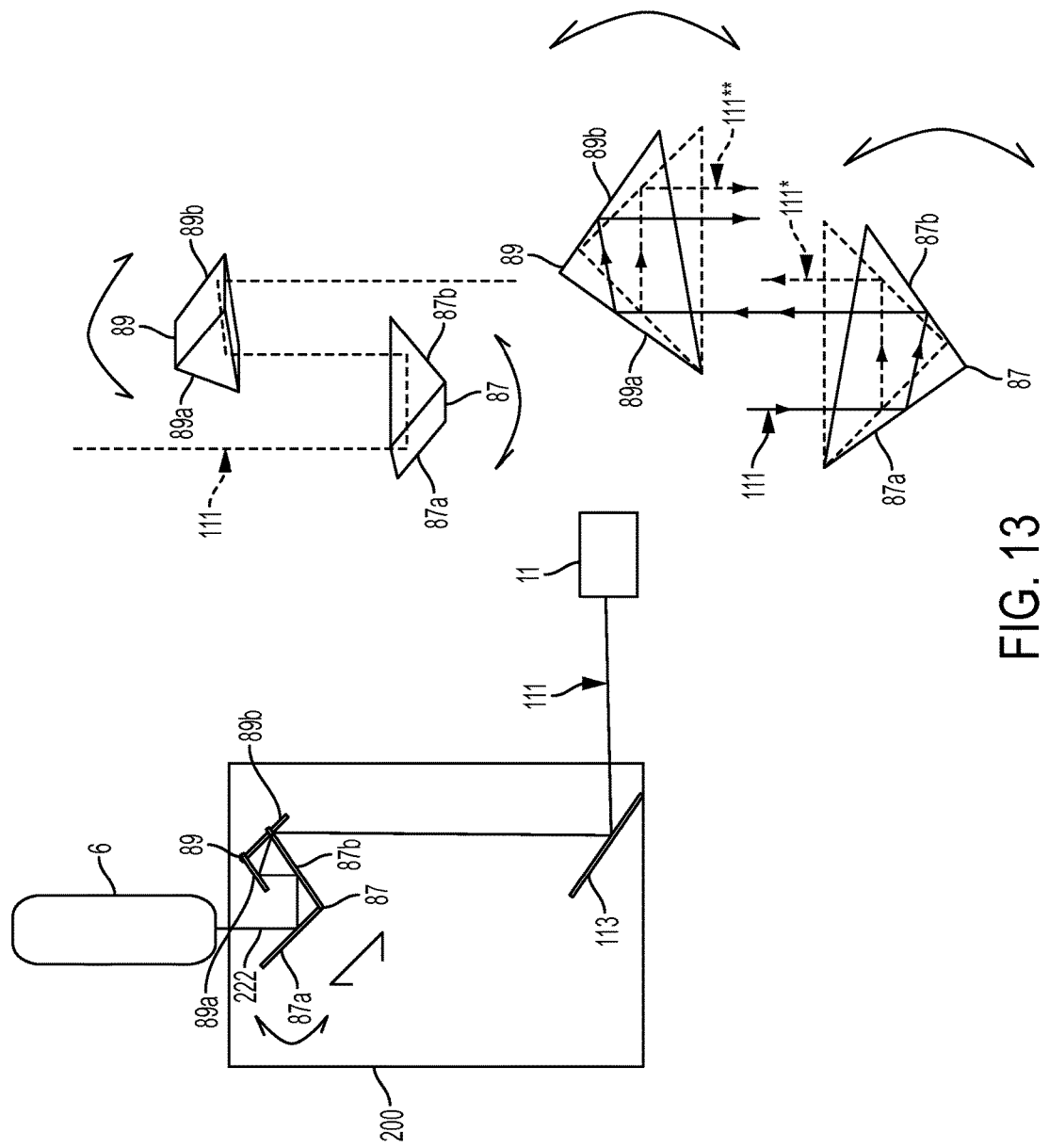
FIG. 13 is a schematic illustration of a beam pattern generator comprising an erector prism, according to one embodiment of the present invention.

FIG. 13 is a schematic diagram of another embodiment of the beam pattern generator 200. In this embodiment, the beam pattern generator 200 includes an erector means i.e. an optical device capable of turning the optical beam 222 by 180 degrees in two different directions so that the image of each individual point of light generated when the optical beam 222 passes through the beam pattern generator 200 is vertically inverted and laterally reversed. Such erector means usually involve a prism or a group of prisms so that an image is inverted in one direction or the other by 90 degrees each time it is reflected off one of the prism reflective surfaces. After reflecting off four perpendicular prism reflective surfaces the optical beam 222 is turned 180 degrees vertically and laterally.

FIG. 13 shows two movable right angled prisms, a first prism 87 with two perpendicular reflective surfaces 87a and 87b and a second prism 89 with two perpendicular reflective surfaces 89a and 89b. The two prisms 87, 89 are oriented perpendicular to each other in a double Porro prism configuration. When the prism 87 rotates, the optical beam 222 hits different parts of the reflective surfaces 87a and 87b so that they reflect the optical beam 222 at the same angle in the horizontal axis but displace it in the horizontal direction and hit the reflective surface 89a and 89b of prism 89 at different areas. Movement of prism 89 in the vertical direction will cause the optical beam 222 to hit different areas of the surfaces 89a and 89b so that the optical beam 222 is reflected at the same angle but displaced to a parallel path in the vertical direction. The movements of both prism 87 and 89 are controlled by the processor 300 to direct the optical beam 222 to different positions on the mirror 113, the lens 15 and the target 11 as disclosed herein. The prisms 87 and 89 can be replaced by mirrors that are configured at right angles to each other.

Figure 14:
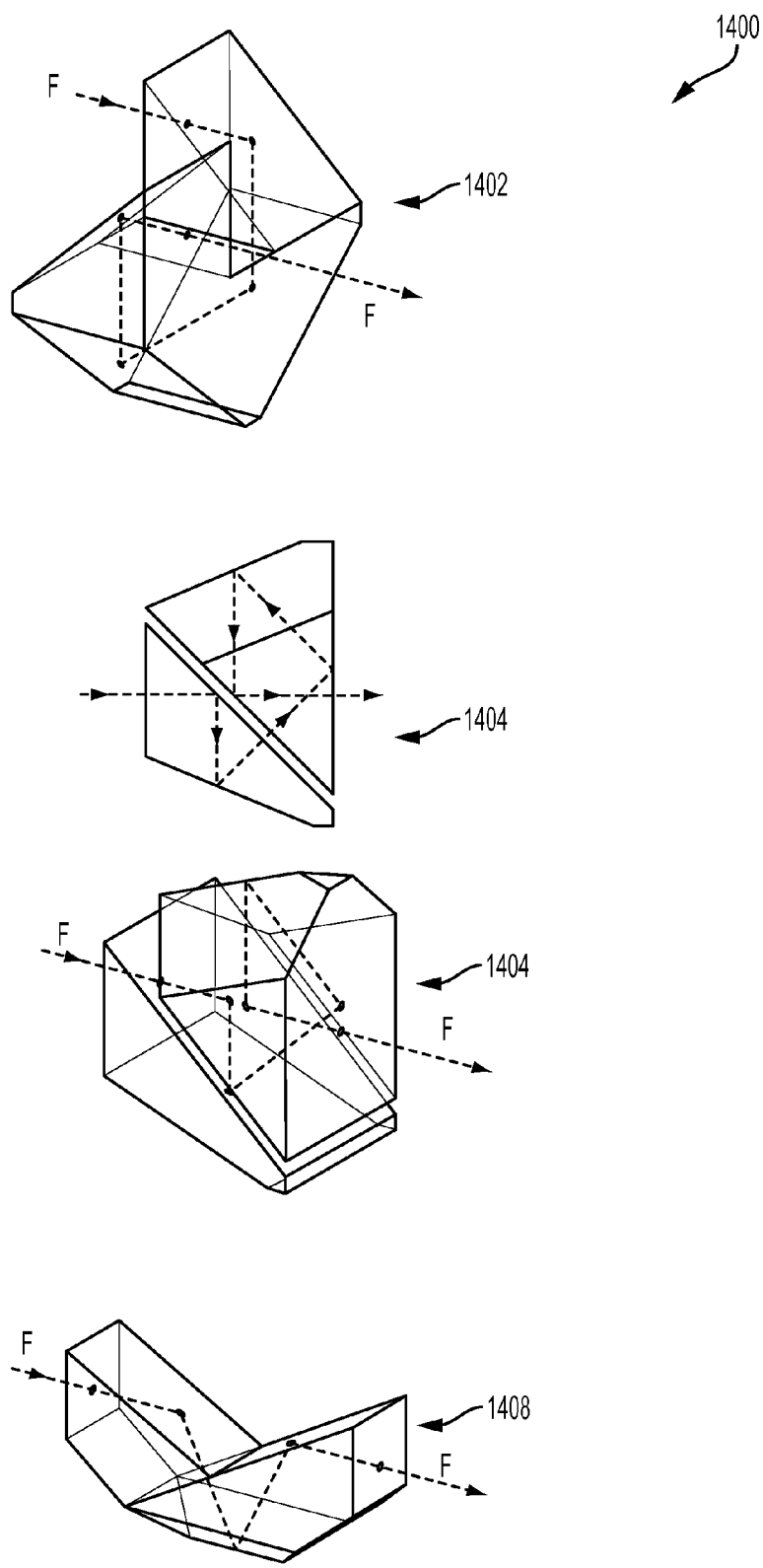
FIG. 14 is a schematic illustration of a subset of prisms, according to one embodiment of the present invention.

FIG. 14 shows three other prisms 1400 (Porro-abbe 1402, Schmidt-pechan 1404, and Abbe-koenig-prisms 1408) and or mirror configurations that are commonly employed to erect an image by utilizing four or more reflective surfaces. Any of such prisms or mirror combinations can be used as an alternative to the double porro prism configuration mentioned herein in the beam pattern generator 200 to achieve the same two dimensional displacements of the optical beam 222 by rotating such prisms in two perpendicular directions.

Figure 15:
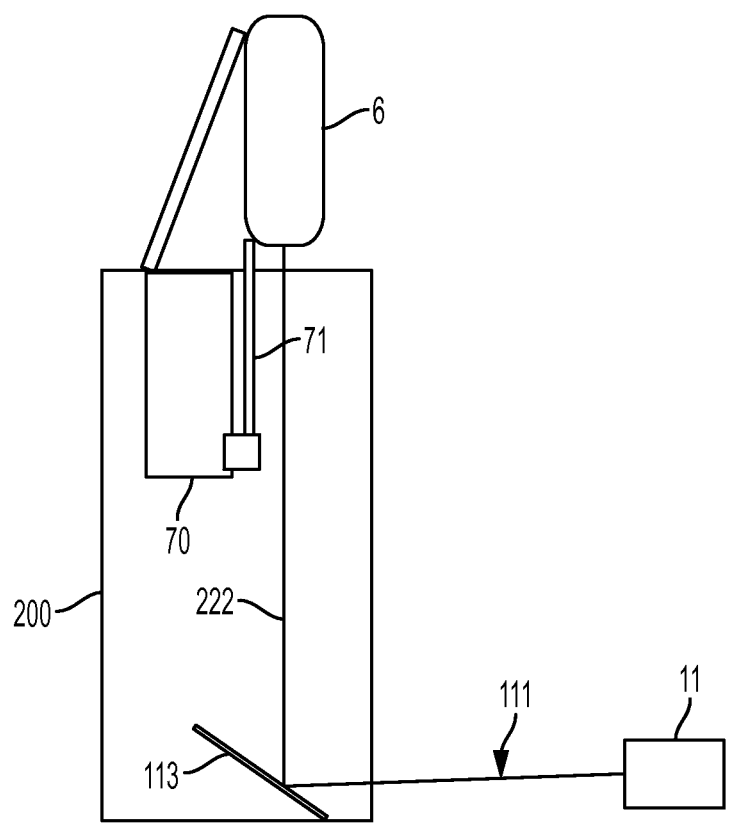
FIG. 15 is a schematic illustration of a beam pattern generator utilizing a movable laser unit to change the angle of the beam, according to one embodiment of the present invention.

FIG. 15 is a schematic diagram of another embodiment of the beam pattern generator 200. In this embodiment, the beam pattern generator 200 includes a moving stage 70 connected to the laser diode assembly 6 mechanically via the lever 71. The moving stage 70 may be configured to move both in the vertical and horizontal directions. As the stage 70 moves along the horizontal direction, the movement is conducted via the arm 71 to the laser diode assembly 6 that in turn, turns in the horizontal direction causing a similar change in the direction of optical beam 222. Similarly a vertical movement of the stage 70 causes a movement of the arm 71 then the laser diode assembly 6 to cause change in the optical beam 222. The optical beam 222 coming from the laser diode assembly 6 hits different points of the mirror 113.

Figure 16:
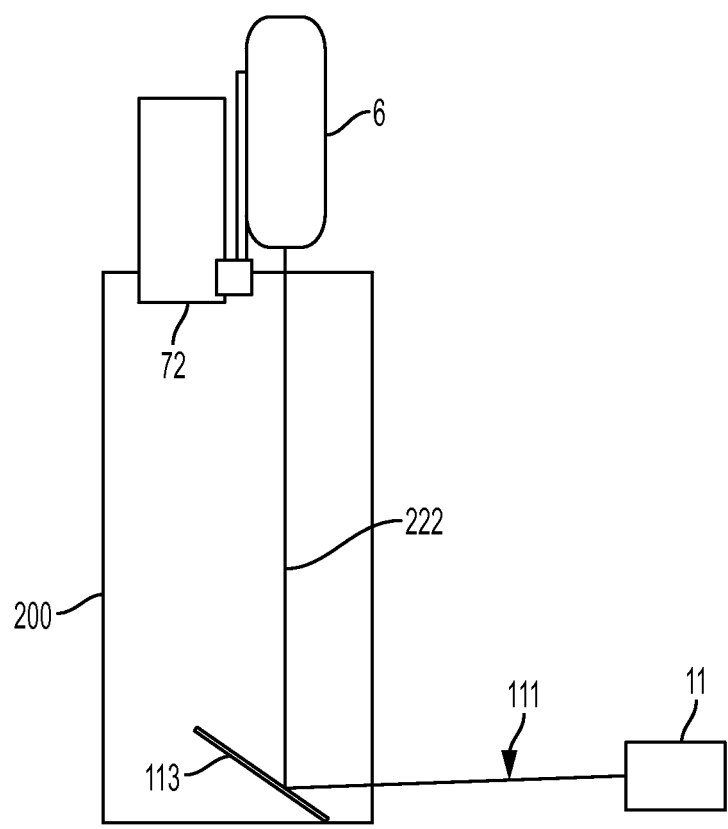
FIG. 16 is a schematic illustration of a beam pattern generator utilizing a movable laser unit to displace the beam, according to one embodiment of the present invention.

FIG. 16 is a schematic diagram of another embodiment of the beam pattern generator 200. In this embodiment, the beam pattern generator 200 includes a moving stage 72 on which the laser diode assembly 6 is mounted. The moving stage 72 may be configured to move both in the vertical and horizontal directions. As the stage 72 moves along the horizontal direction, the laser diode assembly 6 moves along with it, and that in turn turns in the horizontal direction causing a displacement of the optical beam 222 in the horizontal direction. Similarly a vertical movement of the stage 72 causes a movement of the laser diode assembly 6 to cause a vertical displacement in the optical beam 222. The optical beam 222 coming from the laser diode assembly 6 hits different points of the mirror 113.

Figure 17:
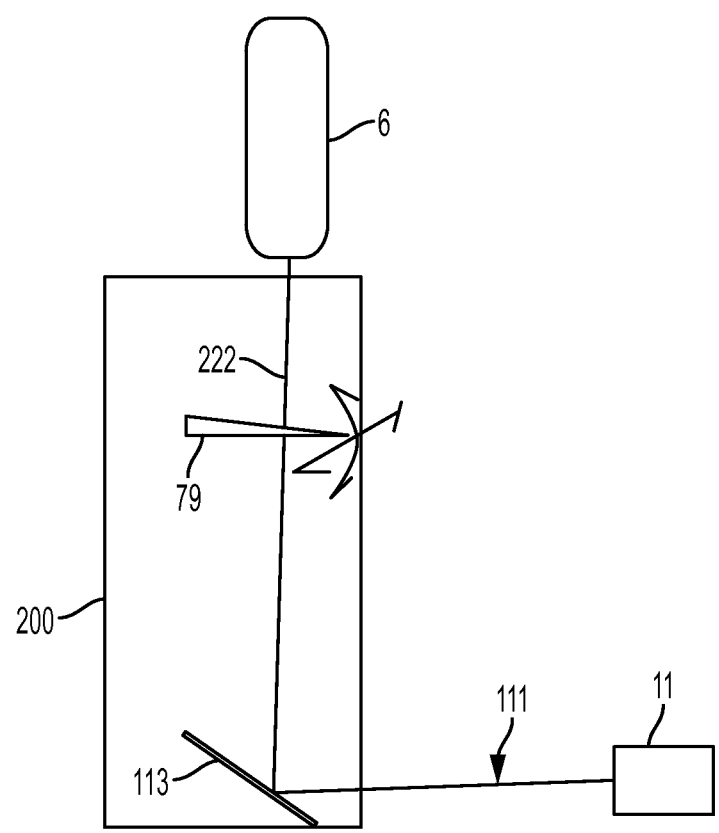
FIG. 17 is a schematic illustration of a beam pattern generator comprising a rotating prism, according to one embodiment of the present invention.

FIG. 17 is a schematic diagram of another embodiment of the beam pattern generator 200. In this embodiment, the beam pattern generator 200 includes a rotatable prismatic element 79, with an axis of rotation parallel to the incidencing optical beam 222. The prismatic effect affected by thus rotating the rotatable prismatic element 79 results in displacement of the optical beam 222 in the vertical and/or horizontal directions relative to the original optical beam 222. By prismatic effect, what is meant is the ability of the optical element to refract the light rays so that the light beam deviates in one direction. For example a rotatable prismatic element that includes a 10 prism diopter oriented at 90 degrees with respect to the incidencing optical beam 222 i.e. base down and apex up, will deviate the optical beam 222 towards the base of the rotatable prismatic element 79 (in the vertical direction) so that it will be displaced 10 cm at a distance of one meter from the prismatic element with no horizontal deviation. If the rotatable prismatic element 79 is rotated by 45 degrees about an axis disposed between the apex and the base of the prism, it will have a resultant power of $10 \times \sin(45)$ vertically direction i.e. 7.1 cm vertically and $10 \cdot \cos(45)$ in the horizontal direction i.e. 7.1 cm horizontally. The progressive rotation of the rotatable prismatic element 79 over 2, 3, 4, 5 or 6 steps will generate a diagonal linear pattern of points of light in the alignment pattern 444.

Additionally the rotatable prismatic element 79 is tilt-able i.e. movable perpendicular to its longitudinal axis so that the angle of incidence of the optical beam 222 on a first surface of the rotatable prismatic element 79 can be changed. This affects a change in direction of optical beam 222 in the vertical direction, i.e. perpendicular to the aforementioned displacement direction. The optical beam 222 coming from the laser diode assembly 6 reaches different parts of the rotatable prismatic element 79 thus getting deviated in the horizontal and vertical axes differently depending on the angle of rotation of the rotatable prismatic element 79. The movement of rotatable prismatic element 79 is controlled by the processor 300 to direct the optical beam 222 to different positions on the mirror 113, the lens 15, and the target 11. As would be appreciated by one of skill, the alignment pattern 444 results.

Figure 18:
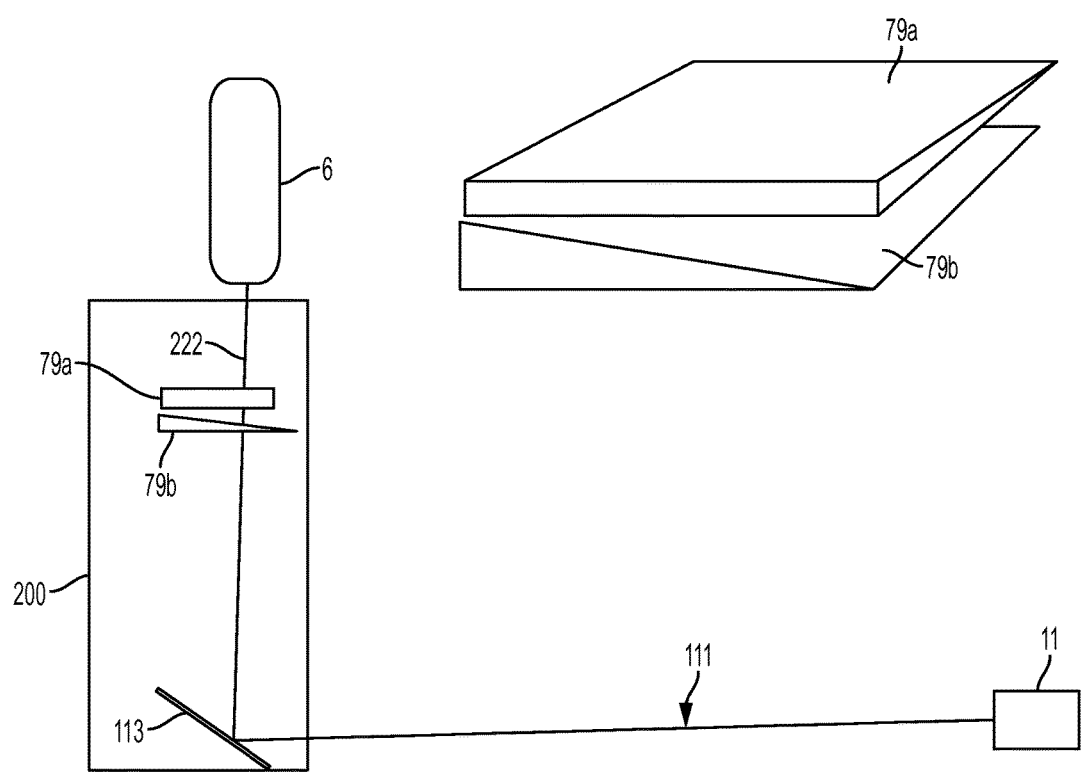
FIG. 18 is a schematic illustration of a beam pattern generator comprising two rotating prisms, according to one embodiment of the present invention.

FIG. 18 is a schematic diagram of another embodiment of the beam pattern generator 200. In this embodiment, the beam pattern generator 200 includes a first rotatable prismatic element 79a and a second rotatable prismatic element 79b configured perpendicular to the optical beam 222. The second rotatable prismatic element 79b has the same prismatic power or a different prismatic power as the first rotatable prismatic element 79a. The rotatable prismatic element 79a rotates its prismatic effect in the vertical and horizontal directions as disclosed in the example of the 10 prism diopter example herein. The rotatable prismatic element 79b rotates in an opposite direction to that of rotatable prismatic element 79a. This allows the rotatable prismatic element 79b to neutralize at least a portion of the horizontal and/or vertical displacement of the optical beam 222 produced by the rotatable prismatic element 79a. For example if the rotatable prismatic element 79a rotates 5 degrees while the rotatable prismatic element 79b rotates 5 degrees in the opposite direction, the optical beam 222 would be displaced in only one direction. The movements of the rotatable prismatic element 79a and the rotatable prismatic element 79b are controlled by the processor 300 to direct the optical beam 222 to different positions on the mirror 113, the lens 15, and the target 11.

FIGS. 19A-19D each show a schematic diagram of another embodiment of the beam pattern generator 200. In each of these embodiments, shown in accordance with aspects of the present invention, the beam pattern generator 200 includes at least a set of movable mounts, a first movable mount 73a and a second movable mount 73b. The first movable mount 73a carries the laser diode assembly 6 module and is capable of moving side to side horizontally, as shown for example in FIG. 19B. The second movable mount 73b carries the reflective element, for example the reflective mirror 113, and is movable in a vertical direction perpendicular to the axis of movement of the first movable mount 73a, as shown in FIG. 19C. The optical beam 222 originates from the laser diode assembly 6 mounted on the first movable mount 73a, which directs the optical beam 222 toward the reflective mirror 113. As the first movable mount 73a moves horizontally, the optical beam 222 is displaced horizontally into a path 111" parallel to the optical path 111, an example of which is shown in FIG. 19B. As the second movable mount 73b moves vertically in a perpendicular direction to the optical beam 222, the optical beam 222 is reflected vertically along a different displaced optical path 111''', an example of which is shown in FIG. 19C. The optical beam 222 reflected along the optical path 111" and/or the optical path 111" is reflected toward the image of the target 11 provided by lens 15 as shown in FIG. 5. When the timing of the laser pulses is coordinated with the position of the first movable mount 73a and/or the second movable mount 73b, separate beams (i.e., multiple points of light) are created. However, as disclosed herein, if the laser emitting diode 66 of the laser diode assembly 6 is left to run continuously, a likewise continuous pattern may be created. Additionally, the first movable mount 73a may carry more than one diode assembly such as 6a and 6b (FIG. 19D). The first movable mount 73a can move horizontally by a distance equal to the distance between the laser diode assembly 6a and the laser diode assembly 6b so that the user can choose which diode assembly is used. For example, if the user selects to use a certain wavelength via the control panel, the processor 300 sends signals to move the first movable mount 73a so that the laser diode assembly (6a) producing the selected wavelength is facing the reflective element, e.g. the reflective mirror 113, attached to the second movable mount 73b. The processor 300 can send signals to both the first movable mount 73a and the second movable mount 73b to generate a pattern as above. When the user selects a different wavelength, the control panel sends signals to move the first movable mount 73a so that diode assembly (6b) is facing the reflective mirror 113. A pattern is generated in a similar way as above.

Figure 20:
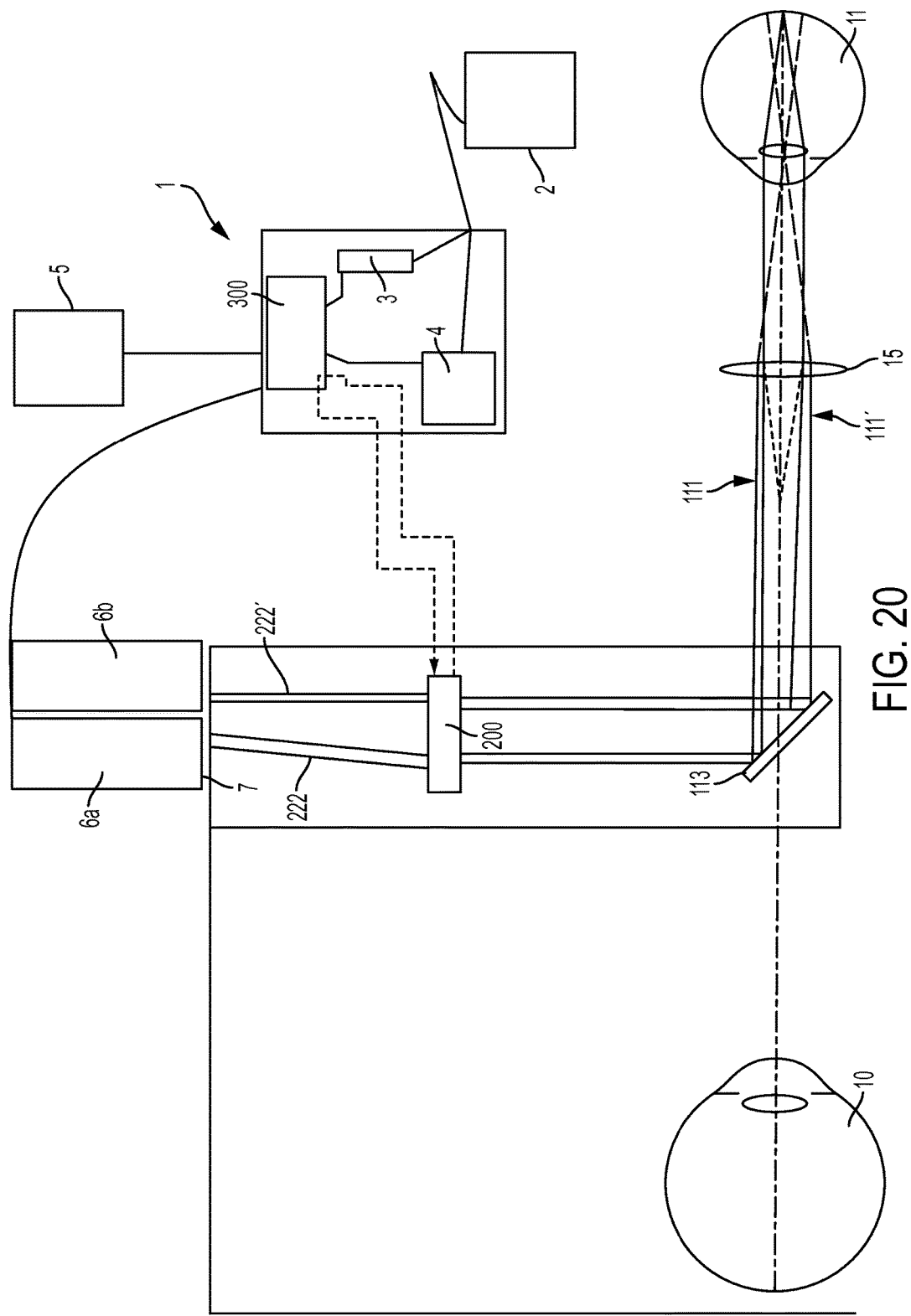
FIG. 20 is a schematic illustration of a compact surgical apparatus comprising more than one laser emitting diode as the laser source, according to one embodiment of the present invention.

In accordance with yet another embodiment of the present invention, as illustrated in FIG. 20, a first laser diode assembly 6a and a second laser diode assembly 6b (or a plurality of laser diode assemblies) is attachable to the beam pattern generator 200 in such a way as to enable the optical beams 222 and 222' directed along optical paths 111 and 111' respectively and the anterior focal point of the operating optical system 20 to be confocal.

The operator determines the wavelength selected for aiming and treatment which in turn activates the laser emitting diodes 66. The laser emitting diodes 66, can be the same or different. There may be separate power regulators 3, one for each laser diode assembly 6a, 6b, or a single power regulator 3 used by one laser diode assembly 6a, 6b at a time, as disclosed herein. As disclosed herein, the electric current from the power source 2 passes to the laser unit 1 through the power regulator 3 to generate with laser diode assembly 6a the aiming light beam and/or to generate with laser diode assembly 6b the aiming light beam. In an embodiment, aiming light beam is in the green wavelength range and aiming light beam is in the red wavelength range. However, as one of skill would appreciate, a plurality of wavelength ranges can each be used for aiming light beams.

Laser emitting diode(s) 66 produce aiming beams of subthreshold energy level either simultaneously or sequentially. In operation, the first laser emitting diode 66 produces the aiming light beam while the second laser emitting diode 66 is producing the aiming light beam and while any additional laser emitting diodes are producing any additional aiming light beams at the same time. When the multiple laser emitting diodes 66 (and any additional laser emitting diodes) are used simultaneously, multiple simultaneous optical beams and exit the laser diode assemblies 6a, 6b, etc. simultaneously, generating multiple points of light at the same time. An alignment pattern 444 of low energy points of light are projected simultaneously onto the target 11.

In an illustrative mode of operation, the laser emitting diode 66 can produce the aiming light beam while the laser emitting diode 66 and any additional laser emitting diodes are off; then the laser emitting diode 66 and any additional laser emitting diodes are off while the laser emitting diode 66 is on, and so on. In this mode of operation, an alignment pattern 444 of low energy points of light are projected sequentially onto the target 11. The optical system of the beam pattern generator 200 is be used to scan the multiple light beams onto the target 11 in one or two directions through the lens 15.

As disclosed herein, the timer circuit 4 is supplied with electric current from the power source 2. When the timer circuit 4 is activated, a predetermined adjustable pulse, or train of pulses, of relatively high current is supplied to the laser diode assembly 6a or 6b to produce a pulse of treatment laser beam 85 at the wavelength(s) selected for treatment. According to an embodiment of the present invention, the characteristic of the laser pulse(s) depend(s) on the pre-determined pulse settings, as would be understood by those of ordinary skill in the art. As noted herein, a separate timer circuit 4 may be used for each laser diode assembly 6a, 6b, or the same circuit may be used on one laser diode assembly 6a, 6b at a time. At the conclusion of the each treatment laser beam 85 pulse, the laser emitting diode emission level returns back to the baseline aiming light beam supplied by the power regulator 3. The compact surgical system 20 has a number of rheostats or switches to control the intensity and duration of the treatment laser beam pulse.

The optical beam 222, 222' emitted from each laser diode assembly 6a, 6b along optical path 111, 111' passes through the laser outlet assembly 7, which directs and controls the size and focus of the exiting optical beams 222, 222'. The laser outlet assembly 7 includes a lens 15 through which the laser energy passes, and a highly reflective mirror 113 to direct the laser beam.

Figure 21:
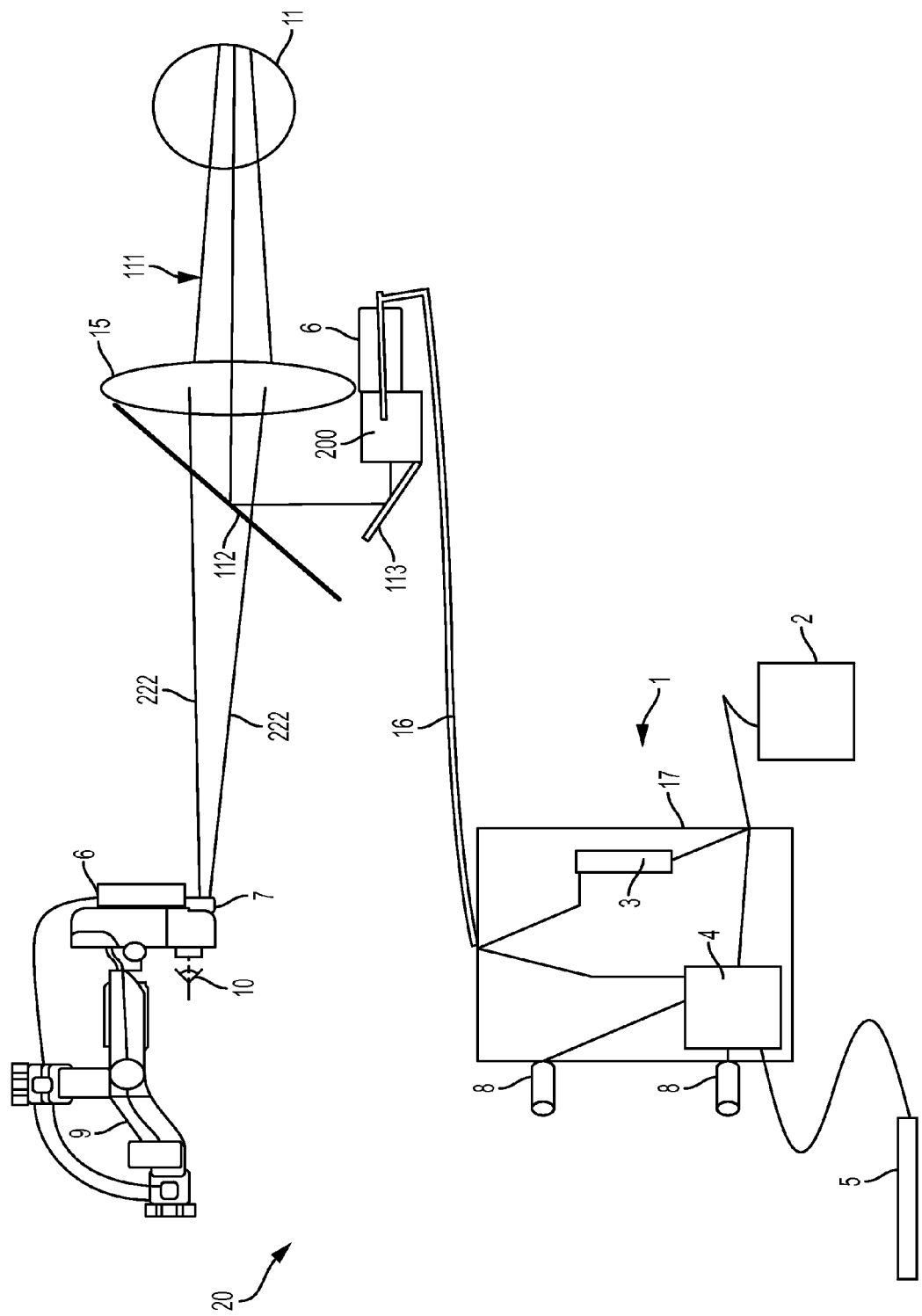
FIG. 21 is a schematic illustration of a compact surgical apparatus comprising a laser diode assembly attached to a lens that is freely movable relative to the user, according to one embodiment of the present invention.

FIG. 21 shows an embodiment of the compact surgical system 20 whereby the laser diode assembly 6 is attached to the lens 15. In some embodiments, a plurality of laser diode assemblies, 6a, 6b, 6c, etc. can be attached to the lens 15.

The laser diode assembly 6 generates the optical beam 222 (including the aiming light beam and/or treatment laser beam) exiting the laser outlet assembly 7 and passing through the beam pattern generator 200 where the optical beam 222 is multiplied and reflected by the mirror 113 towards the dichroic reflective mirror 112. The dichroic reflective mirror 112 reflects light in a specific range of wavelength(s) while allowing light of other wavelengths to pass. The reflective properties of the dichroic reflective mirror 112 are selected so that it will only reflect a narrow range of wavelengths (approximately +/−50 nm) around the peak intensity (for example, 405±50 nm, 445±50 nm, 635±50 nm, 658±50 nm, 7±50 nm or 520±50 nm) of the laser emitting diode 66 of the laser diode assembly 6. The optical beam 222 will be almost completely reflected towards the lens 15 and then the target 11. The light coming off the optical operating system 9 will go through the dichroic reflective mirror 112 with only a small percentage of light being reflected, but the majority of optical beam 222 beam passes through the lens 15 to illuminate the target 11, enabling superimposition of the illuminating light beam onto the aiming light beam and the treatment laser beam such that each of the illuminating light beam, the aiming light beam and the treatment laser beam can be projected into the target 11. The laser diode assembly 6 is connected to the laser unit 1 controlling the current from power source 2 in a similar way as is described herein. The compact control unit 17 controls the beam pattern generator 200 in a similar way as is described herein. As one of skill will recognize, a plurality of beam pattern generator 200 systems (as disclosed herein) and/or methods of use (as disclosed herein) can be implemented according to an embodiment of the present invention.

Continuing with FIG. 21, a comparative spectrographic analysis of two laser emitting diodes is shown. The top image of FIG. 21 shows the optical output of a laser emitting diode that is driven by a current at or below the threshold level (i.e., sub-threshold current). The optical output is produced by spontaneous emission, and the band is too broad to satisfy the narrow band requirement of a coherent laser. The bottom portion of FIG. 21 shows the optical output of a laser emitting diode that is driven by a current above the threshold level (i.e., supra-threshold current). The optical output is produced by stimulated emission of radiation. Unlike the top image, the band depicted in the bottom image is sufficiently narrow to qualify as the band of a coherent laser. The present invention is useful for a number of ophthalmic indications that previously would have required different wavelengths, and thus numerous laser devices, or more complex multi-laser devices. It is especially effective for those procedures that have previously utilized Krypton, Argon, or infrared 810 nm laser emitting diodes.

Embodiments of the present invention enable faster treatments, whether the pulses of optical energy are delivered simultaneously or sequentially. Simultaneous delivery has the advantage of being faster than sequential delivery, but requires a light source capable of delivering high output power, wherein n is the number of elements in the pattern. Sequential delivery, while being slower than simultaneous delivery, places less demand on the power of the light source and provides flexible adjustment of the ultimate delivery pattern. Both simultaneous and sequential deliveries with the device of the invention significantly reduce the treatment time and the placement precision of the lesions when compared to the manual technique that is conventional today. The eye can be considered stationary for approximately one second, the "fixation time." The number of points of light that can be delivered sequentially in this fixation time is inversely proportional to their pulse duration.

A "pattern," as defined herein is meant to include either the simultaneous or sequential delivery of a plurality of points of light onto a target, such as those shown in FIG. 7. Likewise, "points of light" are herein meant to describe either illumination with a static beam or a moving (scanned) beam. Each beam need not be round, but may be of any shape. For example, a non-circular cross-section laser emitting diode may be used and produce an oval or rectangular point of light. It should be noted that any of the treatment and/or aiming beam generation and control techniques, and/or any of the beam multiplying and/or scanning techniques, described herein can be implemented in combination with and/or incorporated as part of the head mounted operating optical system 9.

FIG. 22 depicts a chart illustrating a spectrographic comparative analysis of two laser emitting diodes, in accordance with aspects of the present invention. Specifically, FIG. 22 depicts comparative spectrographic analyses of two laser diodes. The top graph in FIG. 22 depicts an optical output of a laser diode that is driven by a current at or below a threshold level (i.e., a sub-threshold current). Accordingly, the optical output is produced by spontaneous emission, and the band is too broad to satisfy the narrow band requirement of a coherent laser. The bottom graph in FIG. 22 depicts the optical output of a laser diode that is driven by a current above the threshold level (i.e., a supra-threshold current). The optical output is produced by stimulated emission of radiation. Unlike the top graph, the band depicted in the bottom graph is sufficiently narrow to qualify as the band of a coherent laser.

Accordingly, a compact laser device and method for ophthalmic procedures is described herein. The laser device and method can be used in ophthalmic surgeries, e.g. performing focal or panretinal photocoagulation. The device is a compact, portable surgical apparatus, including a generator of a laser in the visible spectrum for emitting both an aiming (marker) light beam of relatively low power, and an operating treatment laser beam of relatively high power from at least one laser emitting diode and passing through the same optical elements without using a fiber-optic delivery system. The aiming and treatment laser beams can be multiplied either spatially or temporally to produce a laser point of light pattern) on the targeted tissues. The laser emitting diode can provide continuous or pulsed operating laser without utilizing a mechanical shutter. Utilizing an aiming and treatment laser from the same laser emitting diode minimizes the chances of device failure that happens when the aiming beams and the treatment laser beams are misaligned. Additionally the difference in the wavelengths of the aiming beam and the treatment laser beam are relatively small (5-50 nm) compared to the commercially available laser systems (typically 660 nm red aiming and 532 treatment laser beam with a difference of 128 nm). This proximity of wavelengths in the suggested single laser emitting diode source device minimizes the difference in chromatic refraction and diffraction by different optical elements in the laser system such as the beam pattern generator and handheld lens as both the aiming and treatment laser beams will deviate to the same extent avoiding the aiming/treatment laser beam mismatch.

The laser diode produces an aiming beam while the pattern generator displaces the beam to a different spot then the laser diode is producing a high energy treatment beam to produce the photocoagulation spot then back to low power aiming beam while the pattern generator moves to the net position. This allows selectively using the high power of the laser while applying the laser treatment with no waste of laser energy. This carries the advantages of saving energy, prolonging the longevity of the laser diode, allows passive cooling of the laser diode in between firing the treatment beams.

The laser system is simple, very compact and energy efficient so it is self-contained within the slit lamp attachable laser, laser indirect ophthalmoscope, eye fundus camera or hand held ophthalmoscope. This allows the laser indirect ophthalmoscope, fundus camera or hand-held ophthalmoscope to function as a stand-alone, self-contained laser system rather than a delivery system.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall there-between.

What is claimed is:

1. A system for diagnosing and treating a medical condition of a subject, the system comprising:
    an optical system comprising an illuminating light source;
    a focusing lens disposed to focus light from the illuminating light source onto an inner portion of an eye of a subject;
    a laser unit comprising a laser diode assembly operable with a single laser source, wherein the single laser source emits an aiming light beam and a treatment laser beam from an outlet of the laser unit such that the treatment laser beam effects treatment on the eye of the subject;
    wherein a focal point of the focusing lens and a focal point of the outlet are generally coincident; and
    wherein the optical system and/or the laser unit are operably disposed on a headset apparatus, which is sized, dimensioned, and configured for mounting on the head of a user.

2. The system of claim 1, further comprising an imaging system configured and arranged to receive, capture, display, or combinations thereof, a focusable image of the inner portion of the eye.

3. The system of claim 1, wherein the system is configured to induce a photocoagulation process at a targeted location on the inner portion of an eye.

4. The system of claim 1, wherein the illuminating light source comprises a binocular indirect ophthalmoscope.

5. The system of claim 1, wherein the focusing lens is distal from the headset apparatus and freely moveable relative thereto by a user.

6. The system of claim 1, wherein the focusing lens is disposed within an imaging device comprising an ocular fundus camera.

7. The system of claim 1, wherein the focusing lens is disposed on the headset apparatus.

8. The system of claim 1, wherein the laser unit is operable in the absence of a fiber-optic cable connector.

9. The system of claim 1, wherein the laser diode assembly comprises a plurality of single laser sources, and/or wherein the laser unit comprises a plurality of laser diode assemblies.

10. The system of claim 1, wherein the single laser source comprises a fiber-optic coupled laser diode.

11. The system of claim 1, wherein the wavelength of the aiming light beam and the wavelength of the treatment laser beam differ by less than 50 nm.

12. A system for diagnosing and treating a medical condition of a subject, the system comprising:
- an optical system comprising an illuminating light source;
- a laser unit comprising a laser diode assembly operable with a single laser source, wherein the single laser source emits an aiming light beam and a treatment laser beam that follow generally the same light path such that the treatment laser beam effects treatment on an eye of the subject;
- a focusing lens disposed to focus light onto an inner portion of the eye of a subject;
- wherein the aiming light beam and the treatment laser beam pass through a beam pattern generator; and
- wherein the optical system and/or the laser unit and/or the beam pattern generator are operably disposed on a headset apparatus, which is sized, dimensioned, and configured for mounting on the head of a user.

13. The system of claim 12, wherein each of the aiming light beam and the treatment laser beam is configured to produce a single point of light on the inner portion of an eye, a plurality of discrete points of light on the inner portion of an eye, at least one continuous pattern of light, or combinations thereof, on the inner portion of an eye.

14. The system of claim 12, wherein a point of light produced by the beam pattern generator comprises a round, oval, square or other shaped form projected onto the inner portion of an eye.

15. The system of claim 12, wherein the aiming light beam and the treatment laser beam are generally collimated prior to passing through the beam pattern generator.

16. The system of claim 12, further comprising a control unit and/or remote interface configured to provide a user with control of a position and a characteristic of a pattern of beams exiting the beam pattern generator.

17. The system of claim 12, wherein the beam pattern generator can generate each one of a plurality of selectable patterns; wherein each pattern comprises at least one of a plurality of points of light; wherein an intensity of each one of the plurality of points of light is adjustable via a user interface; and wherein a duration of incidence of each of the points of light upon the inner portion of the eye of a subject is adjustable.

18. A system for diagnosing and treating a medical condition of a subject, the system comprising:
- an optical system comprising an illuminating light source;
- a laser unit comprising a laser diode assembly operable with a single laser source, wherein the single laser source emits an aiming light beam and a treatment laser beam that follow generally the same optical path such that the treatment laser beam effects treatment on an eye of the subject; and
- a beam pattern generator; wherein at least a portion of the aiming light beam and the treatment laser beam engaging with the beam pattern generator and with a focusing lens can be disposed at a plurality of positions on an inner portion of the eye of a subject; and
- wherein the optical system and the beam pattern generator are operably disposed on a headset apparatus, which is sized, dimensioned, and configured for mounting on the head of a user.

19. The system of claim 18, wherein the laser diode assembly comprises a plurality of single laser sources, wherein each single laser source emits an aiming light beam and a treatment laser beam that follow generally the same light path as each other.

20. The system of claim 18, wherein the laser diode assembly is coupled to the focusing lens.

21. The system of claim 18, wherein the beam pattern generator can produce a pattern of light on the inner portion of the eye of a subject, wherein the pattern comprises a plurality of points of light that are generated sequentially.

22. The system of claim 18, wherein the beam pattern generator can produce a pattern of light on the inner portion of the eye of a subject, wherein the pattern comprises a plurality of points of light that are generated simultaneously.

23. The system of claim 19, wherein a first laser diode and a second laser diode produce an aiming beam simultaneously and/or sequentially.

24. A method for diagnosing and treating a medical condition of a subject wherein:
- an inner portion of an eye of a subject is illuminated using an optical system and a laser unit operably disposed on a headset apparatus which is sized, dimensioned, and configured for mounting on the head of a user;
- wherein an aiming light beam and a treatment laser beam are incident on at least one of a plurality of positions on the inner portion of an eye of a subject;
- wherein a position is generally the same for the aiming light beam and the treatment laser beam such that the treatment laser beam effects treatment on the eye of the subject.

25. The method of claim 24, wherein the aiming light beam and the laser treatment laser beam can be multiplied spatially and/or temporally to produce a pattern of points of light on the inner portion of an eye of a subject.

26. The method of claim 24, wherein at least one of a plurality of positions is accessible using a beam pattern generating device and/or a plurality of laser diode sources.

* * * * *